United States Patent [19]

Mathias

[11] 4,444,061

[45] Apr. 24, 1984

[54] FORCE AND TORQUE SENSOR FOR MACHINE TOOLS

[75] Inventor: Richard A. Mathias, Renton, Wash.

[73] Assignee: Camtech Inc., Renton, Wash.

[21] Appl. No.: 362,451

[22] Filed: Mar. 26, 1982

[51] Int. Cl.³ .............................................. G01L 5/16
[52] U.S. Cl. .................................. 73/862.06; 73/104; 73/862.58
[58] Field of Search ............... 73/104, 862.04, 862.05, 73/862.06, 862.54, 862.58, 78

[56] References Cited

U.S. PATENT DOCUMENTS

| | | |
|---|---|---|
| 1,637,676 | 8/1927 | Bohuszewicz et al. .......... 73/862.06 |
| 2,829,516 | 4/1958 | Chiesorin ......................... 73/862.06 |
| 3,602,090 | 8/1971 | Whetham . |
| 3,728,595 | 4/1973 | Adams . |
| 4,078,195 | 3/1978 | Mathias et al. . |

FOREIGN PATENT DOCUMENTS

| | | | |
|---|---|---|---|
| 595020 | 11/1947 | United Kingdom ............. | 73/862.06 |
| 545882 | 2/1977 | U.S.S.R. ........................... | 73/862.06 |

OTHER PUBLICATIONS

Acurex Corporation, Model 1200A Torsion Measurement System, 7/80.
Acurex Corporation, Model 1201A Dual Channel Torque System, 9/80.
Acurex Corporation, Data Couplers, 4/81.

*Primary Examiner*—Charles A. Ruehl
*Attorney, Agent, or Firm*—Christensen, O'Connor, Johnson & Kindness

[57] ABSTRACT

The sensor includes at least one pressure chamber that is filled with an incompressible fluid, a membrane that forms at least one wall of the pressure chamber, a pressure transducer measuring the pressure within the pressure chamber, and a pressure arm whose first end is secured to a machine tool member at a location at which force and torque are to be measured and whose second end bears on the membrane. By appropriately choosing the number and disposition of pressure chambers, membranes, and pressure arms, output signals from the corresponding pressure transducers are related to selected components of transverse force torque, and axial force of the machine tool member. Various embodiments of the sensor for use with machine tools having a rotating tool and machine tools having a stationary tool are disclosed, and techniques are described in which these embodiments can be used to determine the angle between transverse force exerted on the machine tool member and a stationary axis of the machine tool, to determine the plane of transverse loading of the transverse force, and to compensate the pressure measurements in accordance with the determined plane of transverse loading.

39 Claims, 22 Drawing Figures

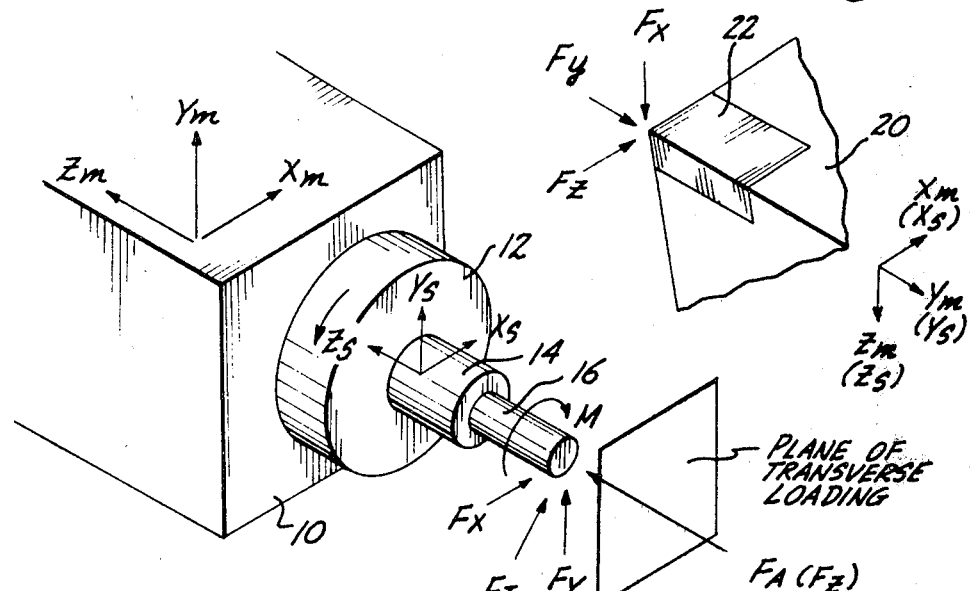
Fig. 1B.
Fig. 1A.
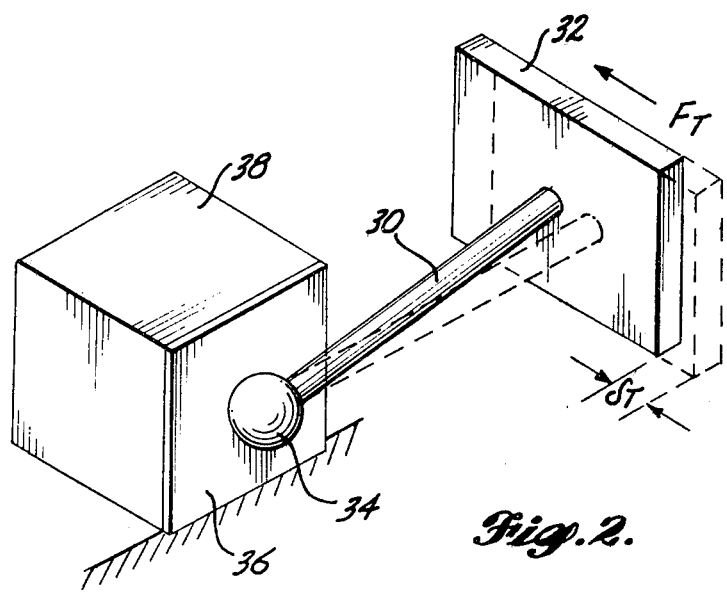
Fig. 2.

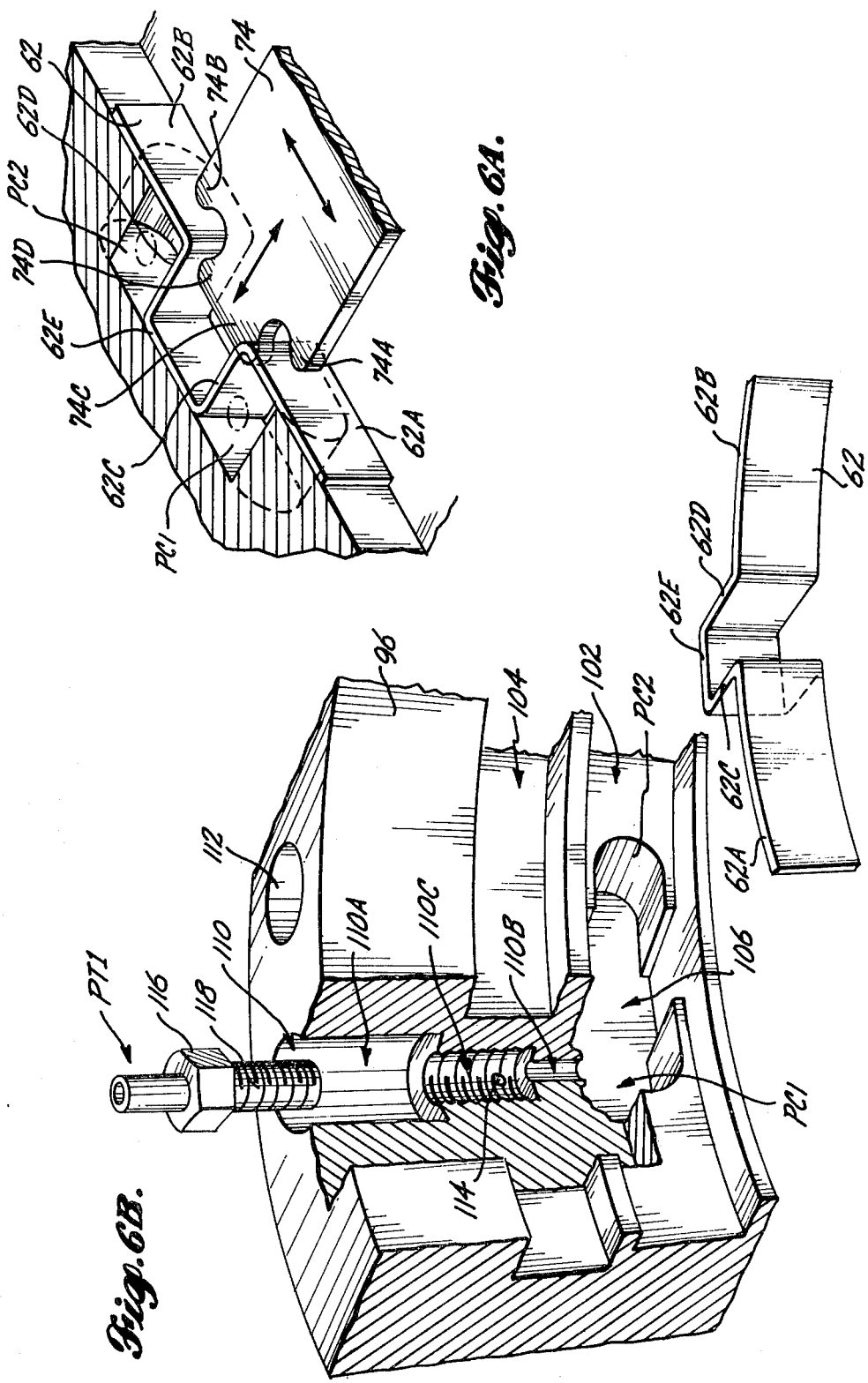

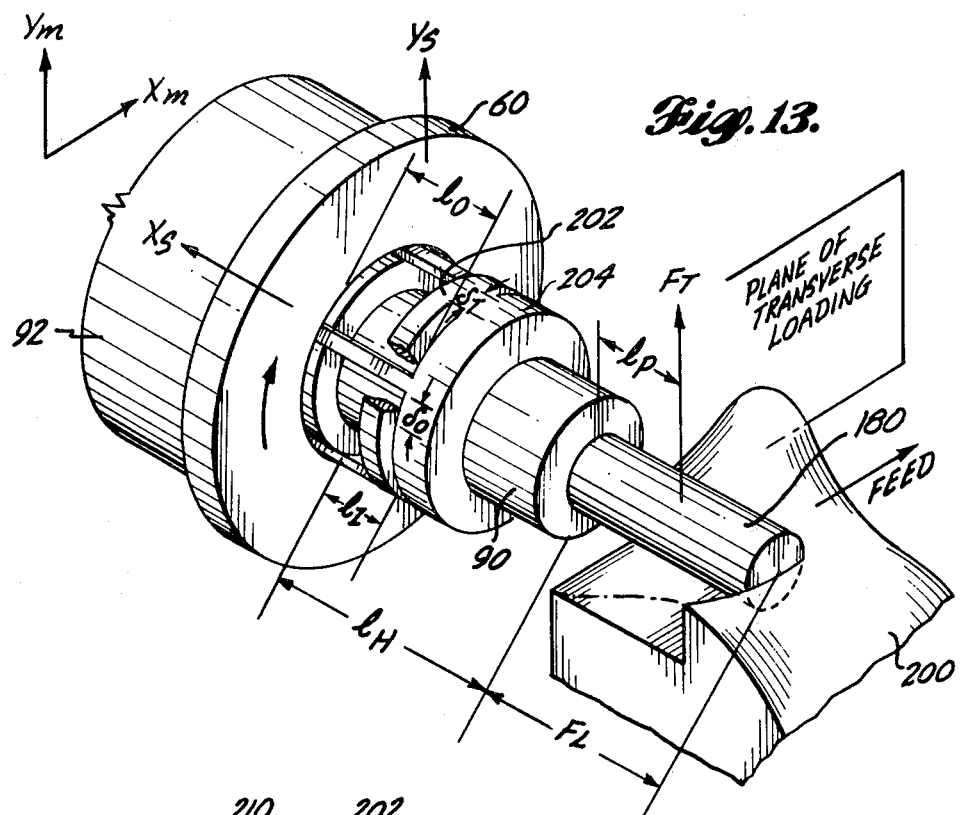
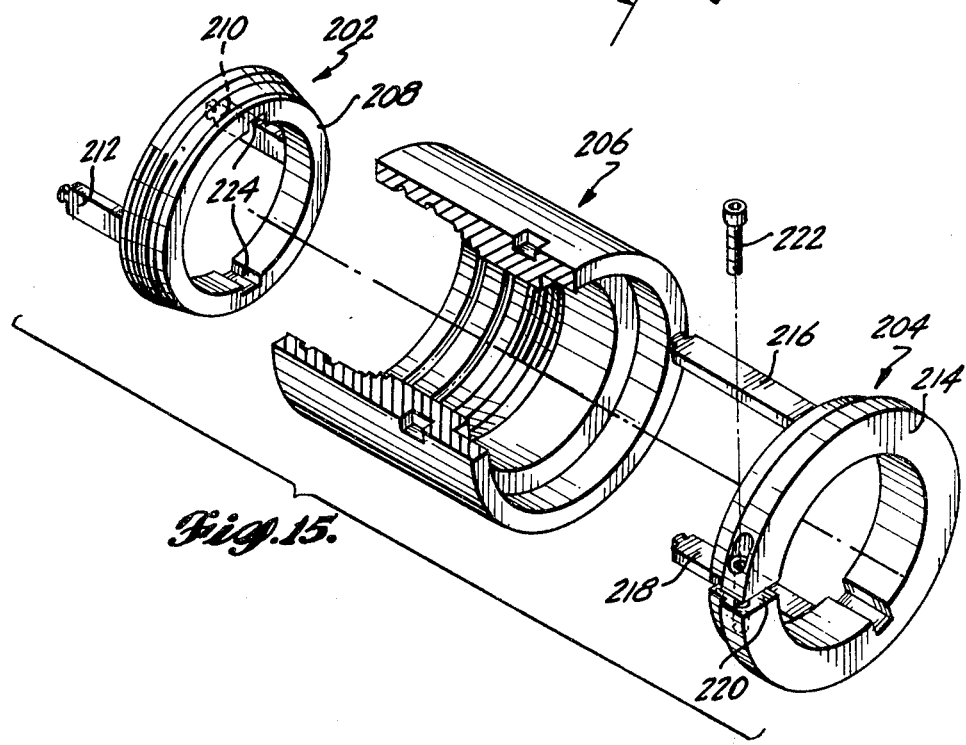

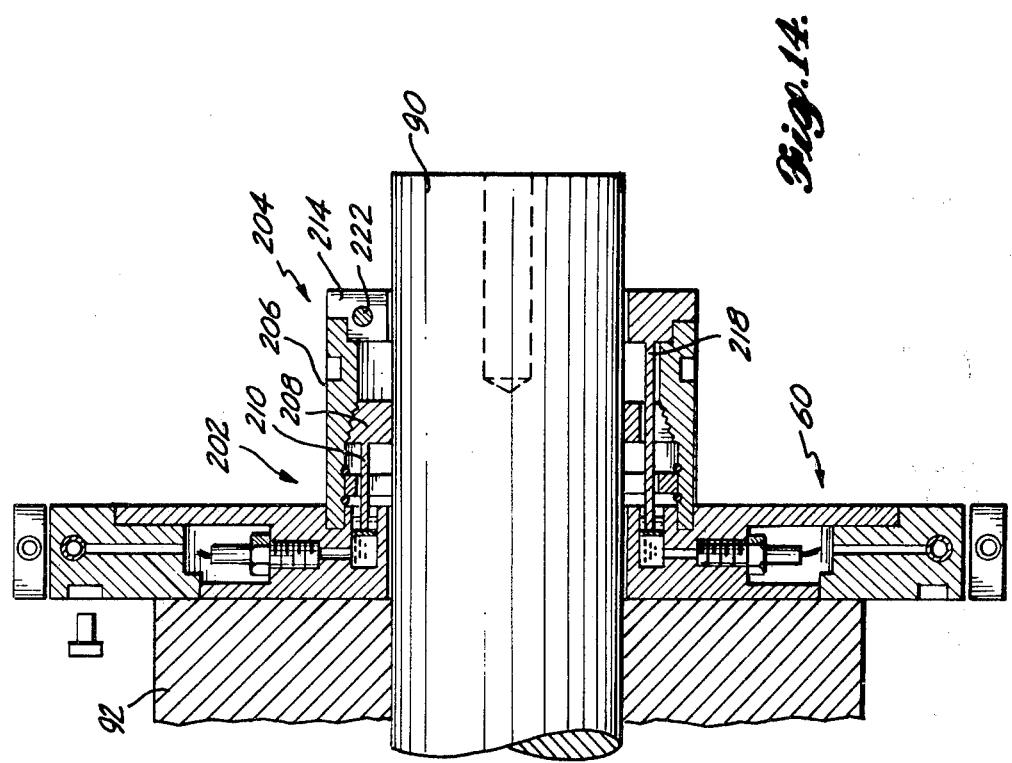

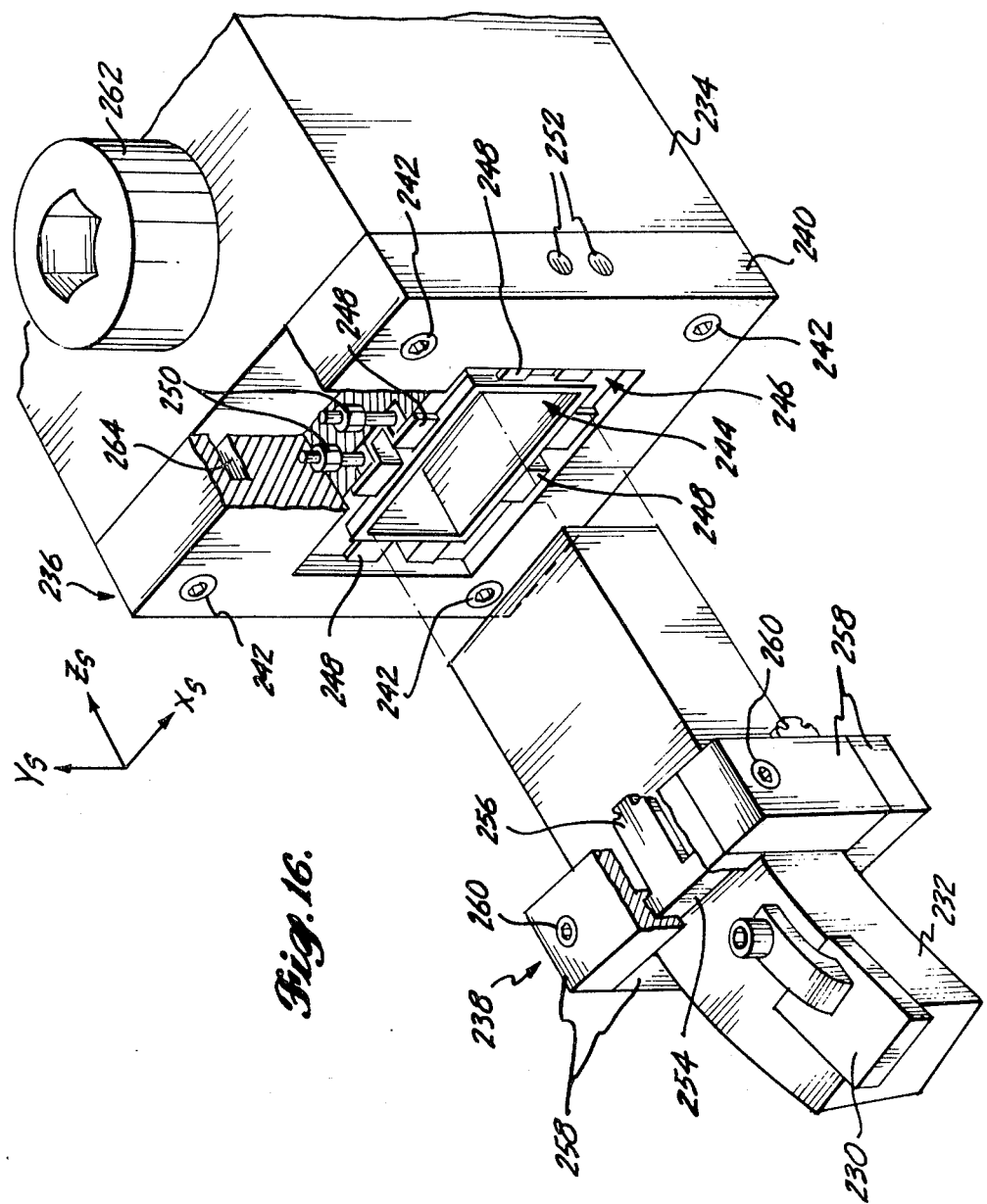

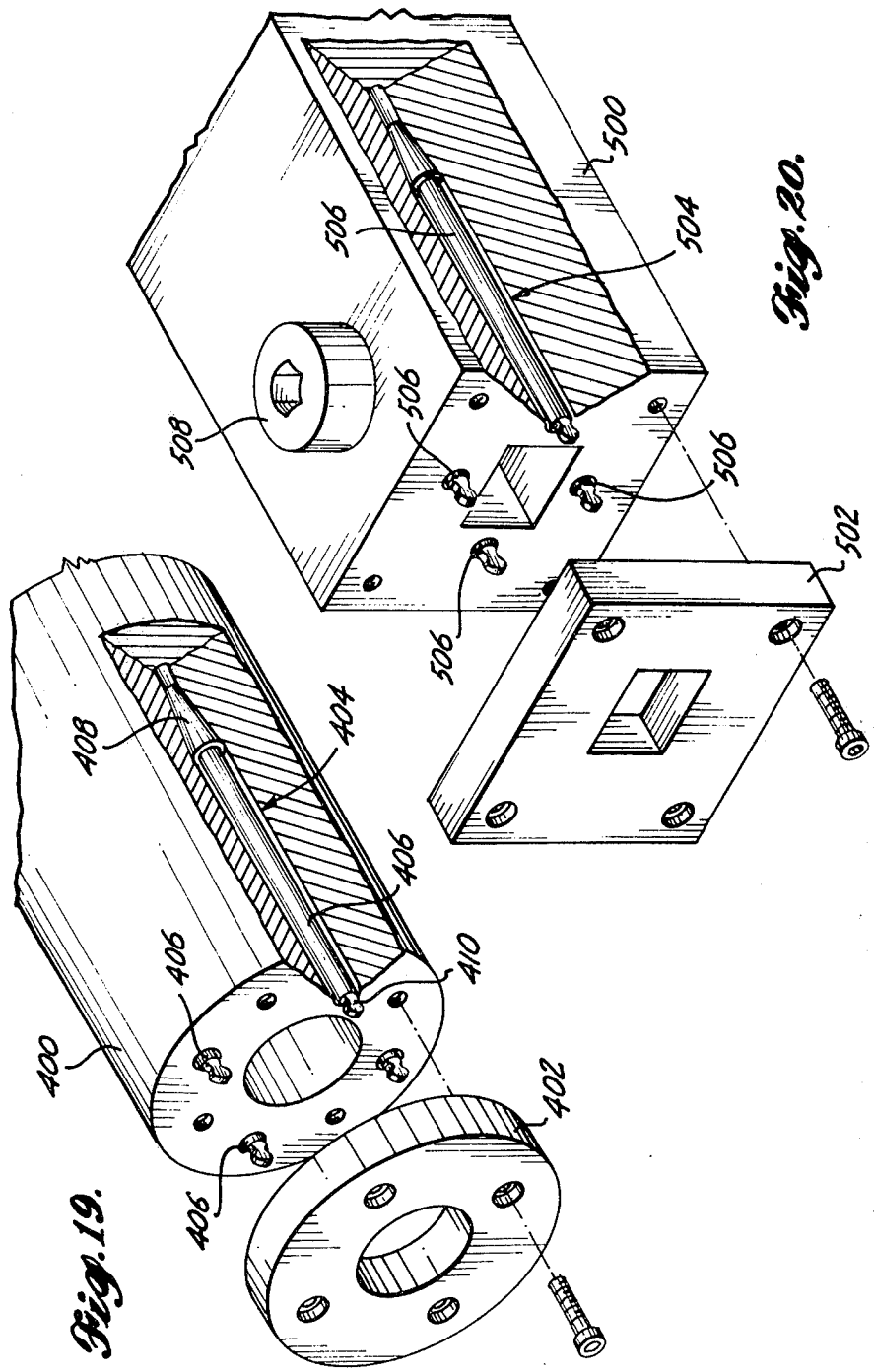

FORCE AND TORQUE SENSOR FOR MACHINE TOOLS

FIELD OF THE INVENTION

This invention generally relates to apparatus and methods for measuring force, torque and displacement, and, more particularly, to a sensor for accurately and precisely measuring the force and torque exerted on and effecting the displacement of a member in a machine tool.

BACKGROUND OF THE INVENTION

Advances in computer technology and in computer-aided manufacturing methods have made possible the design of automated control systems for machine tools that permit the machine tool to meet flexible manufacturing requirements and to be substantially unmanned during operation. The increased cost of labor and energy, the growing shortage of skilled machine tool operators, and the needed increased productivity per machine tool have created a high demand for such automated control systems. To be reliable and productive and yet to be substantially unmanned, these automated control systems monitor various parameters of the machine tool operation to perform adaptive control of the machine tool and to provide diagnostic analysis of the machine tool operation. A typical automated control system can be seen in U.S. Pat. No. 4,078,195, issued Mar. 7, 1978, Adaptive Control System for Numerically Controlled Machine Tools, Mathias et al.

For machine tools having a rotating tool, the parameters usually monitored are the transverse force on the tool (e.g., that force that is transverse to the longitudinal axis about which the tool rotates) which is usually measured in orthogonal x and y directions, the axial force on the tool (e.g., that parallel to the tool axis) which is usually measured in a z direction orthogonal to the x and y directions, and the torque on the tool. These parameters are used for various purposes, such as machine overload protection, tool breakage and vibration detection, tool life and wear monitoring, machining time monitoring, detection of the engagement of the tool with the workpiece, detection of a defective, missing or incorrect tool, and achievement of a maximum rate for the machining operation.

Various types of apparatus and methods have been used in the past to measure transverse force, axial force, and torque. Considering now machine tools having a rotating tool, the tool is mounted in and rotatable with a tool holder that in turn is mounted in and rotatable with a spindle that is supported by bearings in a carriage of the machine and that is rotated by a spindle-drive motor. The workpiece is mounted on a table that is moved in an x direction by an x-drive motor, and the carriage is moved in y and z directions relative to the workpiece by respective y-drive and z-drive motors.

The most common technique used to measure the transverse force on the tool is by measuring reactive displacements of the spindle in the x and y directions. An example of a sensor using this technique can be seen in U.S. Pat. No. 3,602,090, issued Aug. 31, 1971, Milling Machine Control System and Milling Force Sensor Therefor, Whetham, in which a plurality of magnetic transducers are mounted on the carriage in proximity to and about the periphery of the spindle. By appropriately positioning the magnetic transducers and by connecting the magnetic transducers in appropriate bridge arrangements, electrical signals may be obtained that are proportional to x and y displacements of the spindle and that are therefore related to the x and y forces exerted on the tool. The accuracy of this type sensor in converting measured displacements into measured forces is limited, however, by a number of factors such as the quality of the spindle bearing, the consistency and symmetry of the spindle stiffness, the amount of runout or eccentricity that the spindle exhibits during rotation, and temperature. The sensitivity of this type of sensor also changes with variations in the distance from the point at which the transverse load is applied (or, the "plane of loading") to the front of the spindle, so that special procedures must be used in calibrating the sensor and in programming the associated machine tool to accommodate the different planes of loading that are encountered during a machining operation.

Another technique for the measurement of transverse forces is that seen in U.S. Pat. No. 3,728,595, issued Apr. 17, 1973, Feed Rate Control System for Milling Machines, Adams, in which a plurality of strain gauges are mounted either on an adapter between the tool holder and the spindle or directly on the spindle itself. By appropriately mounting the strain gauges and by connecting the strain gauges in appropriate bridge arrangements, electrical signals may be obtained that are proportional to the strain in the tool holder in the x and y directions and that are therefore related to the x and y forces exerted on the tool. To date, practical implementation of this technique has not been achieved because of its cost and because of the hostile environment in which the reliability of the strain gauges must be ensured.

Another technique for the measurement of transverse forces is to measure the torque produced by the x-drive and y-drive motors. In order to measure torque, the power consumed by the motor is measured (by a watts transducer), as is the motor speed, and the measured power is then divided by the measured speed in order to obtain measured torque. While this technique provides adequate force measurements in the case of relatively large and steady-state torque values, the sensitivity of this technique is limited (e.g., torques less than three percent of the maximum torque available usually cannot be resolved) and the time or frequency of this technique is also limited by a number of factors such as friction, acceleration, and the limited frequency response of the watts transducer (e.g., about five Hz).

Still another technique for the measurement of transverse forces is to mount a precision dynamometer between the workpiece and the table which moves the workpiece. The dynamometer includes a plate which has formed therein a number of weakened sections or "beams" that have strain gauges mounted thereon. Although this technique can provide accurate and precise transverse force measurements with good time or frequency response, it is not practical for machining operations because the dynamometer is costly and has a very limited range of workpiece sizes and weights that can be used.

Techniques for the measurement of axial force on a rotating tool are generally similar to those previously described. For example, axial force can be measured by a displacement sensor having magnetic transducers disposed in proximity to the spindle, by strain gauges mounted on the spindle, by measuring the torque of the z-drive motor, or by a precision dynamometer interposed between the workpiece and the table. These techniques for the measurement of axial force are subject to the disadvantages previously noted of similar techniques for the measurement of transverse force. Measurement of torque on a rotating tool is commonly made by measuring the torque of the spindle motor or by strain gauges mounted on the spindle, tool holder, or an adapter therebetween. These techniques of torque measurement are also subject to the disadvantages previously noted.

Considering now machine tools having a stationary tool (such as a lathe), the tool is mounted in a tool holder that in turn is mounted on a tool post, and the tool post is moved in three orthogonal directions relative to the workpiece by associated drive motors. The workpiece is mounted on and rotatable with a spindle which in turn is rotated by an associated drive motor. The parameters usually monitored during a machining operation are the forces along the three orthogonal directions in which the tool post is moved. The most common technique for the measurement of these forces is by the use of a precision dynamometer similar to those previously described that is mounted between the tool holder and the tool post, and another technique that is used is to mount strain gauges directly on either the tool holder or the tool post. These techniques are subject to the disadvantages of high cost, low reliability, and limitation on the range of tool or tool holder sizes and weights similar to those previously discussed.

As can be appreciated from the foregoing discussion, many of the various techniques that have been described can be used to directly or indirectly measure lateral and angular displacements of a member of the machine tool (for example, the lateral displacement of a spindle upon application of a transverse or axial force to the spindle or the angular displacement of the spindle in response to torque exerted on the spindle). The displacement measurements made by use of such techniques, however, are also subject to all of the disadvantages previously noted in conjunction with transverse and axial force measurements and torque measurements.

Very accurate and precise measurements of the lateral and angular displacements of a member of a machine tool can be made by the use of laser interferometers, but such a technique is extremely costly and is suitable only for laboratory and quality testing purposes.

SUMMARY OF THE INVENTION

The invention resides in a sensor responsive to displacement of a first machine tool member for measuring the force and torque exerted thereon, wherein substantially all of the load on the first machine tool member is borne by a second machine tool member of the machine tool. The machine tool may be any machine that uses a tool to perform work, and the first machine tool member may comprise any member of such a machine that is subject to force, torque, or displacement.

The sensor comprises:

first means adapted to be mounted in proximity to the first machine tool member, the first means including: a first pressure chamber that is filled with an incompressible fluid; a membrane of a rigid material that forms at least one wall of the first pressure chamber; and, means measuring the pressure within the first pressure chamber;

an elongated pressure arm of a rigid material; and, means for affixing a first end of the pressure arm to the first machine tool member at a location along the longitudinal axis thereof at which force and torque are to be measured so that a second end of the pressure arm bears on the membrane in the first means.

In one form of the sensor, the first means includes means for affixing the first means to a second machine tool member that is disposed at a second location along the longitudinal axis of the first machine tool member. Typical applications of this form of the sensor are a machine tool having a rotating tool in which the first machine tool member is a tool holder and the second machine tool member is a rotatable spindle to which the tool holder is mounted and with which the tool holder rotates, and a machine tool having a stationary tool in which the first machine tool member is a tool holder and a second machine tool member is a tool post to which the tool holder is mounted and relative to which the tool holder is stationary. In another form of the sensor, the first means includes means for affixing the first means to the first machine tool member at a second location along its longitudinal axis. Typical applications of this form of the sensor are a machine tool having a rotating tool in which the first machine tool member is a rotatable spindle, and a machine tool having a stationary tool in which the first machine tool member is a tool post.

Preferably, the pressure arm extends substantially parallel to the longitudinal axis of the first machine tool member. In order that the pressure within the first pressure chamber may be related to axial force exerted on and axial displacement of the first machine tool member, the first means is adapted so that the membrane includes a first portion transversely to the longitudinal axis when the first means is mounted and the second end of the pressure arm is provided with a first portion that bears normally on the first portion of the membrane. In order that the pressure within the first pressure chamber may be related to transverse force and torque exerted on and effecting transverse displacement and angular displacement of the first machine tool member, the membrane is provided with a second portion that extends parallel to the longitudinal axis when the first means is mounted and the second end of the pressure arm is provided with a second portion that bears normally on the second portion of the membrane.

Preferably, the first means also includes a second pressure chamber that is proximate to the first pressure chamber to define a pair of pressure chambers. The membrane includes one portion that forms at least one wall of the first pressure chamber and another portion that forms at least one wall of the second pressure chamber, and the first means includes means measuring the pressure within the second pressure chamber. The pressure arm is accordingly adapted so that its second end bears on both portions of the membrane.

Preferably, the pressure within each pressure chamber is measured by a pressure transducer that provides a corresponding electrical output signal.

In order to provide independent measurements of force and torque relative to orthogonal sensor axes, one of which is parallel to the longitudinal axis of the machine tool member, the first means may be provided with a plurality of pressure chamber pairs and membranes of the type described that are orthogonally disposed about the longitudinal axis of the machine tool member and the sensor may further include a plurality of pressure arms of the type described, each of which bears on the membrane of a corresponding one of the pressure chamber pairs.

Each pressure arm may be external to the machine tool member, in which case the pressure arms are disposed about the periphery of the machine tool member, or may be internal to the machine tool member, in which case the pressure arms are contained in corresponding longitudinal bores in the machine tool member.

BRIEF DESCRIPTION OF THE DRAWINGS

The invention can best be understood by reference to the following portion of the specification, taken in conjunction with the accompanying drawings in which:

FIG. 1A is a schematic representation of a portion of a machine tool having a rotating tool and illustrating the forces and torque to be measured, and FIG. 1B is a schematic representation of a portion of a machine tool having a stationary tool and illustrating the forces to be measured;

FIG. 2 is a schematic representation of the technique of the present invention for measuring transverse force;

FIG. 8 is a plan view corresponding to FIG. 7;

FIG. 13 is a pictorial view of a second embodiment of the sensor in assembly with a spindle, tool holder and spindle;

FIG. 14 is a cross-sectional view of the sensor in FIG. 13 in assembly with the spindle and tool holder;

FIG. 15 is an exploded, pictorial view of the components of a pressure arm member in the sensor of FIG. 13;

FIG. 16 is an exploded, pictorial view of a third embodiment of the sensor in assembly with a tool post, tool holder, and tool of a stationary machine tool;

FIG. 19 is an exploded, pictorial view of another embodiment of the sensor for machine tools having a rotating tool; and FIG. 20 is an exploded, pictorial view of another embodiment of the sensor for machine tools having a stationary tool.

DETAILED DESCRIPTION OF THE PREFERRED EMBODIMENT

Figure 3:
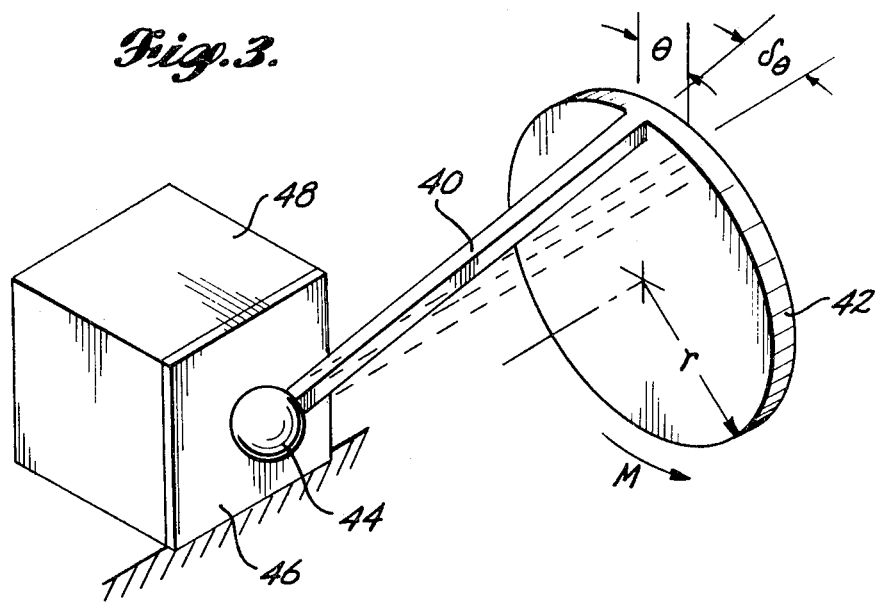
FIG. 3 is a schematic representation of the technique of the present invention for measuring torque.

In FIG. 1A, a machine tool having a rotating tool includes a carriage 10 which has a spindle 12 supported for rotation therein by appropriate bearings (not illustrated). During a machining operation, spindle 12 is rotated in a counterclockwise direction by a spindle-drive motor (not illustrated) within carriage 10. A removable tool holder 14 is mounted in or on spindle 12, and a removable tool 16 is mounted in and rotatable with tool holder 14. As tool 16 engages a workpiece during the machining operation, tool 16 has applied thereto various forces and torques which are to be measured in order to provide suitable input parameters to an automatic control system for the machine tool. These forces and torques are: the *transverse force* $F_T$ applied to tool 16 (that normal to the axis of rotation of tool 16) which includes two orthogonal components $F_x$ and $F_y$; the *axial force* $F_A$ applied to tool 16 (that parallel to the axis of rotation of tool 16) which consists of a single component $F_z$ orthogonal to the plane of $F_x$ and $F_y$ (which plane is sometimes referred to as the *plane of transverse loading*); and, the *torque* M exerted on tool 16 in a direction opposite to the direction of rotation thereof. As will be described in detail hereinafter, the sensor of the present invention is rotatable with spindle 12 and accordingly measures force and torque with respect to three orthogonal *sensor axes* $x_s$, $y_s$, and $z_s$. These sensor axes may be in turn referenced to three orthogonal *machine axes* $x_m$, $y_m$, and $z_m$, with sensor axes $x_s$ and $y_s$ rotating with respect to machine axes $x_m$ and $y_m$ and with sensor axes $z_s$ being aligned with or parallel to machine axis $z_m$.

In FIG. 1B, a machine tool having a stationary tool includes a tool holder 20 and a machining tool 22 mounted in or on tool holder 20, with tool holder 20 and tool 22 being stationary with respect to the portion of the machine tool (a tool post, not illustrated) on which tool holder 20 is mounted. As tool 22 engages a workpiece during a machining operation, the forces to be measured are the transverse forces applied to tool 22 in three orthogonal directions, or, $F_x$, $F_y$, and $F_z$. As described in detail hereinafter, the sensor of the present invention is interposed between tool holder 20 and the tool post and the forces are measured with reference to three orthogonal sensor axes $x_s$, $y_s$, and $z_s$, which in this case are aligned with or parallel to corresponding machine axes $x_m$, $y_m$, and $z_m$.

Figure 4:
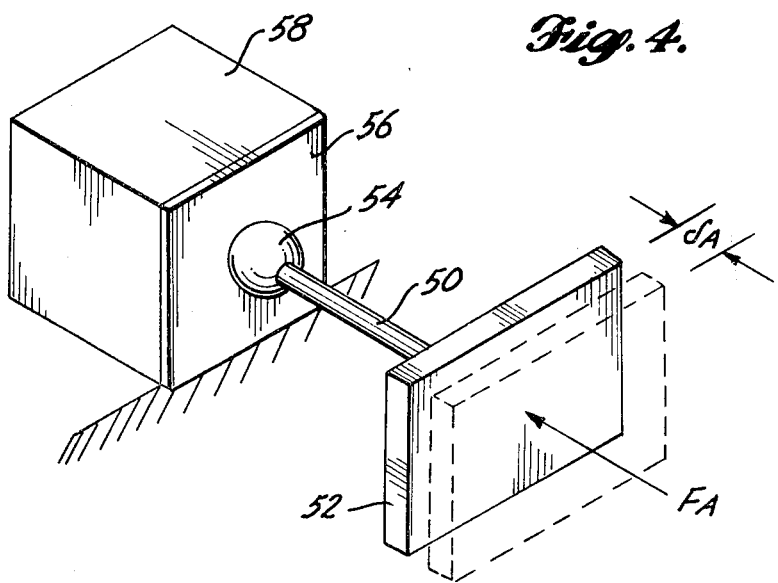
FIG. 4 is a schematic representation of the technique of the present invention for measuring axial force.

The sensor of the present invention uses the technique schematically illustrated in FIGS. 2, 3, and 4 in order to measure transverse force, torque, and axial force.

In FIG. 2, an elongated pressure arm 30 has a first end rigidly attached to a member 32 and a second end bearing (through a sphere 34) on a membrane 36 which forms one wall of a pressure chamber 38 that is filled with an incompressible fluid. A pressure transducer (not illustrated) is mounted within pressure chamber 38 for providing an output signal proportional to the pressure of the fluid within pressure chamber 38. Upon the application of a transverse force $F_T$ to member 32, member 32 undergoes a transverse displacement $\delta_T$ in the direction of the applied force. Substantially all of the transverse displacement $\delta_T$ is taken up in bending of pressure arm 30 and no significant displacement of membrane 36 occurs. However, the pressure within pressure chamber 38 increases in proportion to the magnitude of transverse displacement $\delta_T$ and is reflected in the output signal from the pressure transducer measuring the pressure within pressure chamber 38.

A specific example will now be considered to illustrate the foregoing. Let it be assumed that: pressure arm 30 is a steel rod whose length ($l_a$) is 1" and wherein diameter (D) is ¼"; membrane 36 is a rigid material such as steel, beryllium-copper, aluminum, hard plastic, or hard rubber, as opposed to a semirigid or flexible material such as a soft plastic or a soft rubber, so that membrane 36 does not significantly deform upon application of transverse force to member 32; membrane 36 is thin enough so that its rigidity (in lb/in) is less than ten percent of the transverse rigidity of pressure arm 30; and, the fluid in pressure chamber 38 is incompressible as previously noted.

Given these assumptions, the force $F_{mem}$ exerted on membrane 36 by sphere 34 of pressure arm 30 is:

$$F_{mem} = \frac{3EI_a(\delta_T)}{l_a^3} \quad (1)$$

where:
E = Young's Modulus (for steel, $29 \times 10^6$ lb/in$^2$),
$I_a$ = cross-sectional inertia of pressure arm 30 = $(\pi/64)(D^4)$.

For the specific example under consideration, it will then be seen that:

$$F_{mem} = \frac{3(29 \times 10^6)\left(\frac{\pi}{64}\right)\left(\frac{1}{4}\right)^4 (\delta_T)}{(1)^3} \quad (2)$$

$$= 1.69 \times 10^4 (\delta_T) \quad (3)$$

where: $1.69 \times 10^4$ is the transverse rigidity $R_{transverse}$ in lb/in.

Given the assumption that there is no significant deformation of membrane 36 by sphere 34 of pressure arm 30, it will be seen that the force $F_{mem}$ is uniformly distributed over membrane 36. The pressure $P_{mem}$ on membrane 36 (and therefore the pressure within pressure chamber 38) therefore is:

$$P_{mem} = \frac{F_{mem}}{A_{mem}} \quad (4)$$

where: $A_{mem}$ = surface area of membrane 36.

Assuming that membrane 36 is 3/16" high by 3/16" wide and that the transverse displacement $\delta_T$ is one microinch, it will therefore be seen that:

$$P_{mem} = \frac{1.69 \times 10^4 (1 \times 10^{-6})}{\left(\frac{3}{16}\right)^2} \quad (5)$$

$$= .48 \text{ psi} \quad (6)$$

Therefore, the pressure sensitivity $PS_{\delta T}$ of membrane 36 to transverse displacements (and therefore that of pressure chamber 38) is 0.48 psi per microinch.

In FIG. 3, an elongated pressure arm 40 has a first end rigidly affixed to a member 42 and a second end bearing (through a sphere 44) on a membrane 46 which forms one wall of a pressure chamber 48 that is filled with an incompressible fluid. A pressure transducer (not illustrated) is mounted within pressure chamber 48 for providing an output signal proportional to the pressure within pressure chamber 48. Upon the application of a torque M to member 42, member 42 undergoes an angular displacement $\delta_\theta$ (with $\delta_\theta = r\theta$ where $\delta_\theta$ and r are in inches and $\theta$ is in radians). Substantially all of the angular displacement $\delta_\theta$ is taken up by twisting of pressure arm 40 and no significant displacement of membrane 46 occurs. However, the pressure within pressure chamber 48 increases in proportion to the magnitude of angular displacement $\delta_\theta$ and is reflected in the output signal from the pressure transducer measuring the pressure within pressure chamber 48.

Again considering a specific example, let it be assumed that: pressure arm 40 is a steel bar whose length ($l_a$) is 1", whose width (b) is ⅛", and whose height (h) is ¼"; membrane 46 is of a rigid material; the rigidity of membrane 46 is less than ten percent of the angular rigidity of pressure arm 40; and the fluid within pressure chamber 48 is incompressible.

The forces $F_{mem}$ exerted on membrane 46 by the sphere 44 of pressure arm 40 is:

$$F_{mem} = \frac{3EI_a(\delta_\theta)}{l_a^3} \quad (7)$$

where:
E = Young's Modulus (for steel, $29 \times 10^6$ lb/in),
$I_a$ = Cross-sectional inertia of pressure arm 40 = $(1/12)(bh^3)$.

For the specific example under consideration, it will then be seen that:

$$F_{mem} = \frac{3(29 \times 10^6)\left(\frac{1}{12}\right)\left(\frac{1}{8}\right)\left(\frac{1}{4}\right)^3 (1.5)(\theta)}{(1)^3} \quad (8)$$

$$= 2.12 \times 10^4 (\theta) \quad (9)$$

where: $2.12 \times 10^4$ is the angular rigidity $R_{angular}$ in lb-radian.

Assuming that membrane 46 is 3/16" square and that the force $F_{mem}$ is uniformly distributed across the entire surface of membrane 46, the pressure $P_{mem}$ exerted on membrane 46 (and therefore the pressure within pressure chamber 48) in response to an angular displacement $\theta$ of one microradian is:

$$P_{mem} = \frac{2.12 \times 10^4 (1 \times 10^{-6})}{\left(\frac{3}{16}\right)^2} \quad (10)$$

$$= .603 \text{ psi} \quad (11)$$

Therefore, the pressure sensitivity $PS_\theta$ to angular displacements is 0.603 psi per microradian.

In FIG. 4, an elongated pressure arm 50 has a first end rigidly affixed to a member 52 and a second end bearing (through a sphere 54) on a membrane 56 which forms one wall of a pressure chamber 58 that is filled with an incompressible fluid. A pressure transducer (not illustrated) measures the pressure within pressure chamber 58 and provides an output signal proportional thereto.

Upon the application of an axial force $F_A$ to member 52, member 52 undergoes an axial displacement $\delta_A$. As will be apparent from the following discussion of a specific example, this axial displacement is borne almost entirely by membrane 56 (which correspondingly deforms). The pressure within pressure chamber 58 increases in proportion to axial displacement $\delta_A$ and is reflected in the output signal from the pressure transducer measuring the pressure within pressure chamber 58.

Again considering a specific example, let it be assumed that: pressure arm 50 is steel rod whose length ($l_a$) is 1" and whose diameter (D) is ¼"; membrane 56 is of a rigid material; the rigidity of membrane 56 is less than ten percent the axial rigidity of pressure arm 50; the total axial rigidity $R_{axial}$ of pressure arm 50 and membrane 56 is $1 \times 10^5$ lb/in; and, the fluid within pressure chamber 58 is incompressible.

Given these assumptions, the force $F_{mem}$ exerted on membrane 56 by sphere 54 of pressure arm 50 is:

$$F_{mem} = R_{axial}(\delta_A) \qquad (12)$$

$$= 1 \times 10^5 (\delta_A) \qquad (13)$$

Assuming that membrane 56 is 3/16" square and that the force $F_{mem}$ is uniformly distributed across the entire surface of membrane 56, the pressure $P_{mem}$ exerted on membrane 56 (and therefore the pressure within pressure chamber 58) in response to an axial displacement $\delta_A$ of one microinch is:

$$P_{mem} = \frac{1 \times 10^5 (1 \times 10^{-6})}{\left(\frac{3}{16}\right)^2} \qquad (14)$$

$$= 2.86 \text{ psi} \qquad (15)$$

Therefore, the pressure sensitivity $PS_{\delta_A}$ to axial displacements is 2.86 psi per microinch.

Figure 5:
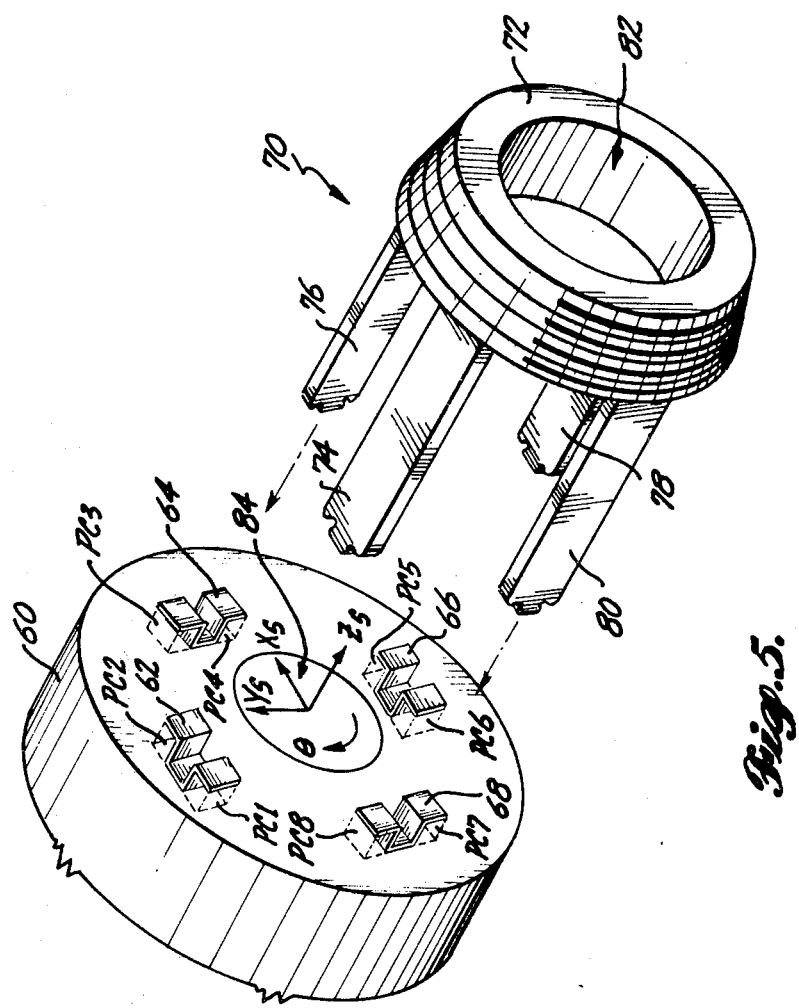
FIG. 5 is a pictorial view of a first embodiment of the sensor or the present invention including a pressure arm member having a plurality of pressure arms that are received in a receptacle module.

A first embodiment of a sensor, for a machine tool having a rotating tool, using the techniques previously described in conjunction with FIGS. 2 through 4 can be seen in FIG. 5.

A receptacle module 60 is mounted on and rotatable with the spindle of the machine tool and has located therein a plurality of pressure chambers PC1 . . . PC8. The pressure chambers are disposed in pairs and the front wall and one sidewall of each of the pressure chambers within a pair are formed by a single membrane mounted in receptable module 60. Accordingly, membrane 62 forms the front wall and one sidewall of pressure chambers PC1 and PC2, membrane 64 forms the front wall and one sidewall of pressure chambers PC3 and PC4, membrane 66 forms the front wall and one sidewall of pressure chambers PC5 and PC6, and membrane 68 forms the front wall and one sidewall of pressure chambers PC7 and PC8. The pair of pressure chambers PC1 and PC2 and the pair of pressure chambers PC5 and PC6 are disposed at separated points along sensor axis $y_s$. Likewise, the pair of pressure chambers PC3 and PC4 and the pair of pressure chambers PC7 and PC8 are disposed at separated points along sensor axis $x_s$. The sidewalls of pressure chambers PC1 and PC2 provided by membrane 62 are opposing and each normal to sensor axis $x_s$, and the sidewalls of pressure chambers PC5 and PC6 provided by membrane 66 are opposing and each normal to sensor axis $x_s$. Likewise, the sidewalls of pressure chambers PC3 and PC4 provided by membrane 64 are opposing and each normal to sensor axis $y_s$, and the sidewalls of pressure chambers PC7 and PC8 provided by membrane 68 are opposing and each normal to sensor axis $y_s$. The front walls of pressure chambers PC1 . . . PC8 provided by membranes 62, 64, 66, and 68 are coplanar and each normal to sensor axis $z_s$.

From the foregoing description, it will be appreciated that the pair of pressure chambers PC1 and PC2 and the pair of pressure chambers PC5 and PC6 can be used to measure transverse forces along sensor axis $x_s$, that the pair of pressure chambers PC3 and PC4 and the pair of pressure chambers PC7 and PC8 can be used to measure transverse forces along sensor axis $y_s$, that all of the pressure chambers PC1 . . . PC8 can be used to measure torque about sensor axis $z_s$, and that all of the pressure chambers PC1 . . . PC8 can be used to measure axial forces along sensor axis $z_s$. As will be discussed in detail hereinafter in conjunction with FIGS. 6A, 6B, 7 and 8, each of the pressure chambers is filled with an incompressible fluid and the pressure therein is measured by a pressure transducer that provides an output signal whose voltage is proportional to the measured pressure.

The sensor also includes a pressure arm member 70 that includes an annular collar 72 and a plurality of orthogonally disposed pressure arms 74, 76, 78, and 80 extending from collar 72. In assembly, the tool holder of the machine tool (which is mounted in or on the spindle of the machine tool) is received within a central aperture 82 of collar 72 and a corresponding central aperture 84 in receptacle module 60. Collar 72 is affixed to the tool holder so that collar 72 is subjected to the transverse displacements, angular displacements, and axial displacements of the tool holder. Also in assembly, the free ends of pressure arms, 74, 76, 78, and 80 engage corresponding membranes 62, 64, 66, and 68 in receptacle module 60.

Figure 6:
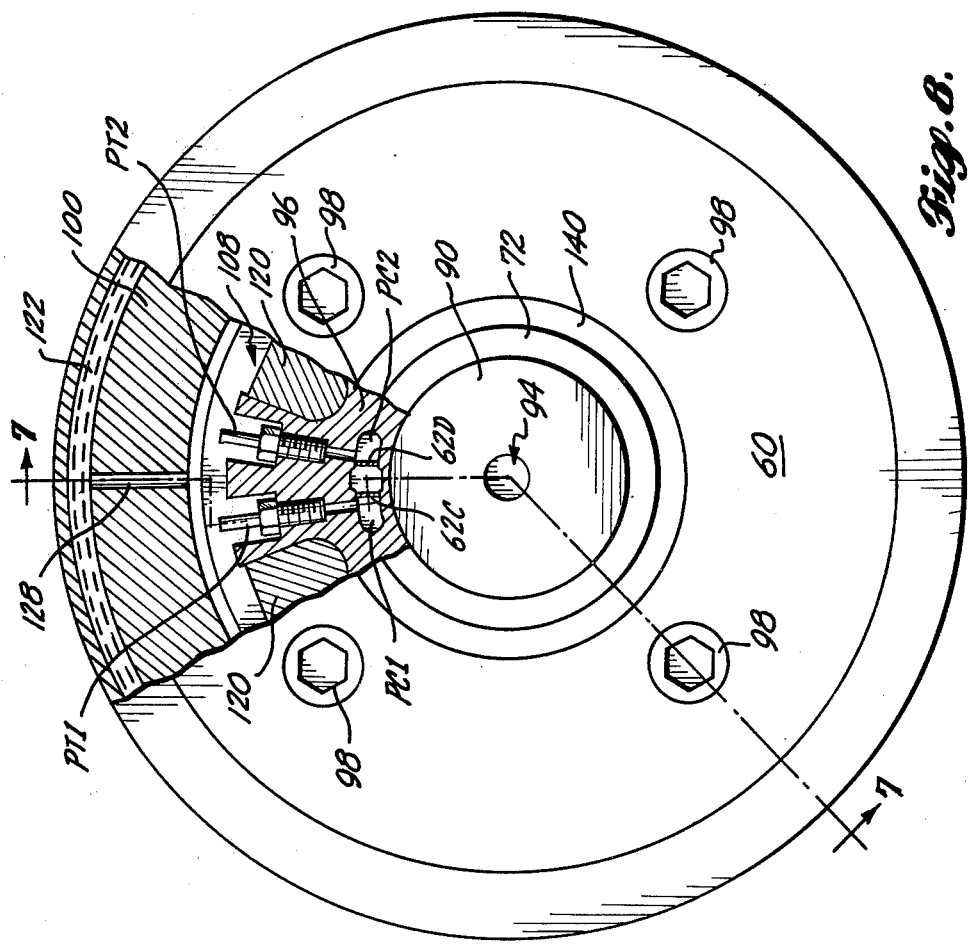
FIG. 6A is a pictorial and partially cross-sectional view illustrating the engagement of one of the pressure arms with a corresponding portion of the receptacle module.
FIG. 6B is a pictorial and partially cross-sectional view of a portion of the receptacle module.

The specific manner in which the free end of each pressure arm engages its corresponding membrane is illustrated in FIG. 6A with reference to pressure arm 74 and membrane 62. At its free end, pressure arm 74 is provided with opposing apexes 74A and 74B that extend parallel to sensor axis $z_s$, and opposing apexes 74C and 74D that extend parallel to sensor axis $x_s$. Apex 74A engages a portion 62A of membrane 62 comprising the front wall of pressure chamber PC1, apex 74B engages a portion 62B of membrane 62 comprising the front wall of pressure chamber PC2, apex 74C enages a portion 62C of membrane 62 comprising the sidewall of pressure chamber PC1, and apex 74D engages a portion 62D of membrane 62 comprising the sidewall of pressure chamber PC2. It will therefore be appreciated that the structure of each pressure arm and its corresponding membrane permits each pressure chamber in the pair of pressure chambers associated with the membrane to be responsive to displacements along two orthogonal sensor axes.

It can be shown that the pressure measurements made by the pressure transducers within the pressure chambers for each type of displacement of pressure arms 74, 76, 78, and 80 in FIG. 5 are independent. To illustrate this point, let it be assumed that: a cumulative output signal $V_x$ is provided that equals the sum of the output signals from the pressure transducers for pressure chambers PC2 and PC5 minus the sum of the output signals from the pressure transducers for pressure chambers PC1 and PC6; a cumulative output signal $V_y$ is provided that equals the sum of the output signals from the pressure transducers PC3 and PC8 minus the sum of the output signals from the pressure transducers for pressure chambers PC4 and PC7; a cumulative output signal $V_z$ is provided that equals the sum of the output signals from the pressure transducers for pressure chambers PC1 ... PC8; a cumulative output signal $V_\theta$ is provided that equals the sum of the output signals from the pressure transducers for pressure chambers PC2, PC4, PC6 and PC8 minus the sum of the output signals from the pressure transducers for pressure chambers PC1, PC3, PC5 and PC7; all pressure chambers are preloaded to some pressure value after member 70 has been assembled with receptacle module 60; and, each cumulative output signal axis is initialized to zero before any displacements occur. Let it further be assumed that the sensitivity of each pressure transducer to a transverse displacement is $K_{tp}$, that the sensitivity of each pressure transducer to an axial displacement is $K_{zp}$, and that the sensitivity of each pressure transducer to an angular displacement is $K_{\theta p}$ (with each sensitivity being expressed in volts/psi so that the output signal from each pressure transducer is equal to the product of the pressure transducer sensitivity and the pressure within the associated pressure chamber).

Considering now sensor axis $x_s$, the initial output signal $V_{x0}$ before a transverse displacement occurs is:

$$V_{x0} = K_{tp}(P_2 - P_1 + P_5 - P_6) = 0 \quad (16)$$

where: $P_1$ is the pressure within pressure chamber PC1, etc.

Upon the occurrence of a transverse displacement along sensor axis $x_s$ which results in a pressure increase $\Delta P$ in two of the four pressure chambers and a corresponding pressure decrease $\Delta P$ in the remaining two of the pressure chambers, the resultant cumulative output signal is:

$$V_x = K_{tp}[(P_2 + \Delta P) - (P_1 - \Delta P) + (P_5 + \Delta P) - (P_6 - \Delta P)] \quad (17)$$

$$= V_{x0} + 4K_{tp}(\Delta P) \quad (18)$$

$$= 4K_{tp}\Delta P \quad (19)$$

Considering now sensor axis $y_s$, the initial output signal $V_{y0}$ before a transverse displacement occurs is:

$$V_{y0} = K_{tp}(P_3 - P_4 + P_8 - P_7) = 0 \quad (20)$$

where: $P_3$ is the pressure within pressure chamber PC3, etc.

Upon the occurrence of a transverse displacement along sensor axis $y_s$ which results in a pressure increase $\Delta P$ in two of the pressure chambers and a corresponding pressure decrease $\Delta P$ in the remaining two of the pressure chambers, the resultant cumulative output signal is:

$$V_y = K_{tp}[(P_3 + \Delta P) - (P_4 - \Delta P) + (P_8 + \Delta P) - (P_7 - \Delta P)] \quad (21)$$

$$= V_{y0} + 4K_{tp}\Delta P \quad (22)$$
$$= 4K_{tp}\Delta P \quad (23)$$

Considering now sensor axis $z_s$, the initial output signal $V_{z0}$ before an axial displacement occurs is:

$$V_{z0} = K_{zp}(P_1 + P_2 + P_3 + P_4 + P_5 + P_6 + P_7 + P_8) = 0 \quad (24)$$

Upon the occurrence of an axial displacement along sensor axis $z_s$ which results in a pressure increase $\Delta P$ in each of the pressure chambers, the resultant cumulative output signal is:

$$V_z = \quad (25)$$

$$K_{zp}[(P_1 + \Delta P) + (P_2 + \Delta P) + (P_3 + \Delta P) + (P_4 + \Delta P) +$$

$$(P_5 + \Delta P) + (P_6 + \Delta P) + (P_7 + \Delta P) + (P_8 + \Delta P)]$$

$$= V_{z0} + 8K_{zp}\Delta P \quad (26)$$

$$= 8K_{zp}\Delta P \quad (27)$$

Considering now angular displacements above sensor axis $y_s$, the initial output signal $V_{\theta 0}$ before an angular displacement occurs is:

$$V_{\theta 0} = K_{\theta p}(P_2 - P_1 + P_4 - P_3 + P_6 - P_5 + P_8 - P_7) = 0 \quad (28)$$

Upon the occurrence of an angular displacement $\theta$ that results in a pressure increase $\Delta P$ in four of the pressure chambers and a corresponding pressure decrease $\Delta P$ in the remaining four pressure chambers, the cumulative output signal is:

$$V_\theta = \quad (29)$$

$$K_{\theta p}[(P_2 + \Delta P) - (P_1 - \Delta P) + (P_4 + \Delta P) - (P_3 - \Delta P) +$$

$$(P_6 + \Delta P) - (P_5 - \Delta P) + (P_8 + \Delta P) - (P_7 - \Delta P)]$$

$$= V_{\theta 0} + 8K_{\theta p}\Delta P \quad (30)$$

$$= 8K_{\theta p}\Delta P \quad (31)$$

From relations (19) and (23), it will be appreciated that the cumulative output signals from the sensor in FIG. 5 for given transverse displacements along sensor axes $x_s$ and $y_s$ are each four times the output signal from a single pressure transducer. From relations (27) and (31), it will be appreciated that the cumulative output signals from the sensor in FIG. 5 for given axial displacements along and angular displacements about sensor axis $y_s$ are each eight times the output signal from a single pressure transducer.

A practical configuration of receptacle module 60 and member 70 for use with a particular type of spindle and tool holder is illustrated in FIGS. 6B, 7, 8 and 9.

A substantially cylindrical tool holder 90 is mounted and rotatable with a spindle 92. Tool holder 90 projects beyond the front face of spindle 92 and has centrally located in its far end a bore 94 that receives a machining tool (not illustrated). Receptacle module 60 is mounted on the front face of spindle 92 and surrounds but is separated from a portion of tool holder 90. Collar 72 of member 70 is fitted around another portion of tool holder 90 that is proximate to the far end thereof, and the various pressure arms of member 70 extend toward and are received in receptacle module 60 as described.

Figure 7:
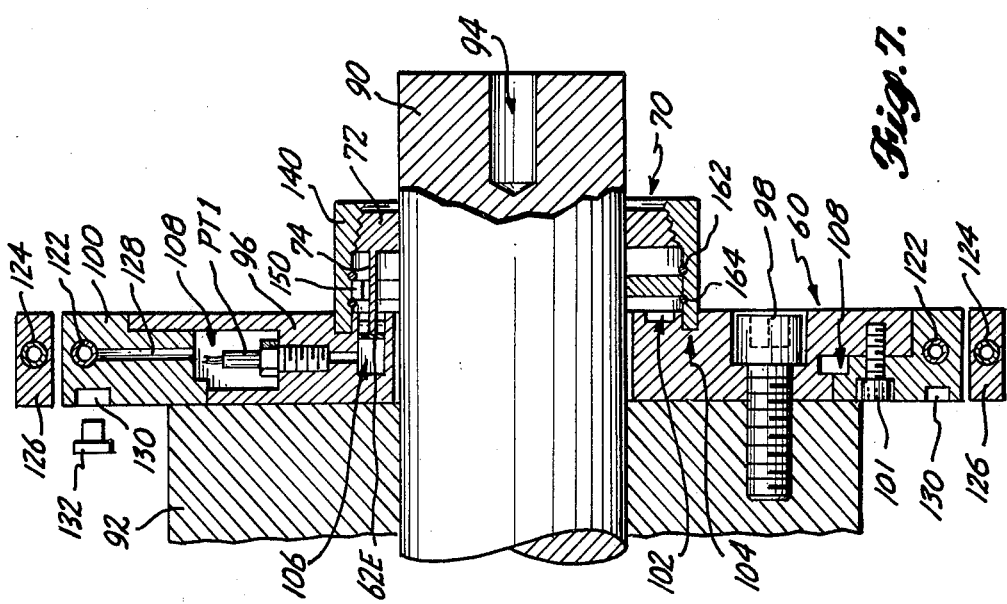
FIG. 7 is a cross-sectional elevation view of the sensor in assembly with a spindle and a tool holder.

Receptacle module 60 includes an inner, cylindrical member 96 that is affixed to the front face of spindle 92 by a plurality of threaded fasteners 98, and an outer, annular ring 100 that is fitted on cylindrical member 96 and that is secured thereto by a plurality of threaded fasteners 101. As best illustrated in FIGS. 6B and 7, annular grooves 102 and 104 are provided on the front face of cylindrical member 96, with groove 104 having a greater diameter than groove 102. At four orthogonally spaced locations along groove 102, recesses 106 extend into cylindrical member 96 from groove 102. The rear, top, bottom, and sidewalls of each recess 106 define corresponding walls of a pair of pressure chambers (e.g., pressure chambers PC1 and PC2 as illustrated in FIG. 6B). As previously described, the remaining sidewalls and the front walls of each pair of pressure chambers are provided by the corresponding membrane. Considering now pressure chambers PC1 and PC2 and specifically referring to FIG. 6B, the rear surfaces of "front wall" portions 62A and 62B of membrane 62 and the rear surface of a central portion 62E of membrane 62 are coated with a suitable adhesive (such as epoxy). By the use of a suitable tool, membrane 62 is inserted into groove 102 so that portions 62C, 62D, and 62E are received within recess 106. The insertion of membrane 62 continues until portions 62A and 62B contact the floor of groove 102 and portion 62E contacts the floor of recess 106, whereupon membrane 62 is maintained at this position by the insertion tool until the adhesive has cured.

Extending along its periphery, cylindrical member 96 is provided with an annular groove 108 (of varying cross-sectional area) as illustrated in FIG. 7. A pair of bores 110, 112 extend from angular groove 108 into each of recesses 106 as illustrated in FIG. 6B. Considering now the bore 110 extending into that portion of the recess 106 defining pressure chamber PC1 (FIG. 6B), it will be seen that bore 110 consists of a large portion 110A adjacent groove 108, a small portion 110B adjacent recess 106, and an intermediate, threaded portion 110C interconnecting portions 110A and 110B. A bleed port 114 extends transversely from intermediate portion 110C to the rear face of cylindrical manner 96. The dimensions of the various portions of port 110 are chosen to accommodate a commercially available pressure transducer such as a semiconductor strain gauge pressure transducer manufactured and sold by Kulite Semiconductor Products, Inc. of Ridgefield, N.J., or piezoelectric pressure transducers manufactured and sold by PCB Piezotronics, of Depew, N.Y. Such pressure transducers are currently available with the pressure sensitivity, thermal stability, frequency response, dynamic range, miniaturization, shock resistance, and ease of mounting required for the sensor of the present invention. A typical example is the Kulite Subminiature pressure transducer, Series Kt-140. In FIG. 6B, pressure transducer PT1 is of this type and includes a nut 116 from which extends a threaded shank 118.

Once the pressure chambers have been defined by installation of the corresponding membranes, the pressure chambers are filled with an incompressible fluid and the pressure transducers are installed in the following manner. Referring again to FIG. 6B, the incompressible fluid is introduced into pressure chamber PC1 through port 110 until the incompressible fluid reaches the level of bleed port 114. Pressure transducer PT1 is then inserted into port 110 and shank 118 thereof is threaded into corresponding intermediate portion 110C of port 110 until the output signal from pressure transducer PT1 indicates a pressure increase, at which time bleed port 114 is sealed.

It will therefore be seen that pressure transducer PT1 measures the pressure within pressure chamber PC1, that a pressure transducer PT1 can be inserted into bore 112 to measure the pressure within pressure chamber PC2, and that pressure transducers PT3 . . . PT8 can be inserted into the remaining bores 110, 112, in order to measure the pressure within pressure chambers PC3 . . . PC8.

The output signals from pressure transducers PT1 . . . PT8 are supplied to a circuit and combined in order to develop signals representing transverse force along sensor axes $x_s$ and $y_s$, axial force along sensor axis $z_s$, and torque, as described hereinafter in conjunction with FIG. 17, and the components of this circuit are contained within a plurality of cavities 120 extending into cylindrical member 96 from annular groove 108, with each of the cavities being filled with a suitable potting compound as illustrated in FIG. 8. The force and torque signals are multiplexed and modulated on an appropriate RF carrier to produce a data signal which is transmitted from receptacle by means of an annular loop antenna 122 embedded in outer ring 100. As illustrated in FIG. 7, the transmitted data signal is received by an annular loop antenna 124 that is embedded in a stationary annular member 126 surrounding the periphery of receptacle module 60, and demultiplexed and demodulated by a circuit as described hereinafter in conjunction with FIG. 18. Electrical connections between pressure transducers PT1 . . . PT8 and the circuit within cavities 120 is made by appropriate electrical leads extending along annular groove 108, and electrical connections between this circuit and loop antenna 122 are made by appropriate electrical leads extending along annular groove 108 and through a radial bore 128 in outer ring 100 extending from annular groove 108 to loop antenna 122.

For the purposes to be described hereinafter, it is also desirable to detect the angular position of receptacle module 60 (and therefore the angular position of sensor axes $x_s$ and $y_s$) relative to a stationary position (such as machine axes $x_m$ and $y_m$,). To this end, an angular position sensor of a photo-optic or inductive type may be used. In FIG. 7, the angular position sensor is of the photo-optic type and includes annular encoded member 130 mounted in the rear face of outer ring 100 and a stationary photo-optic source and detector 132 mounted in proximity to encoded member 130.

Figure 9:
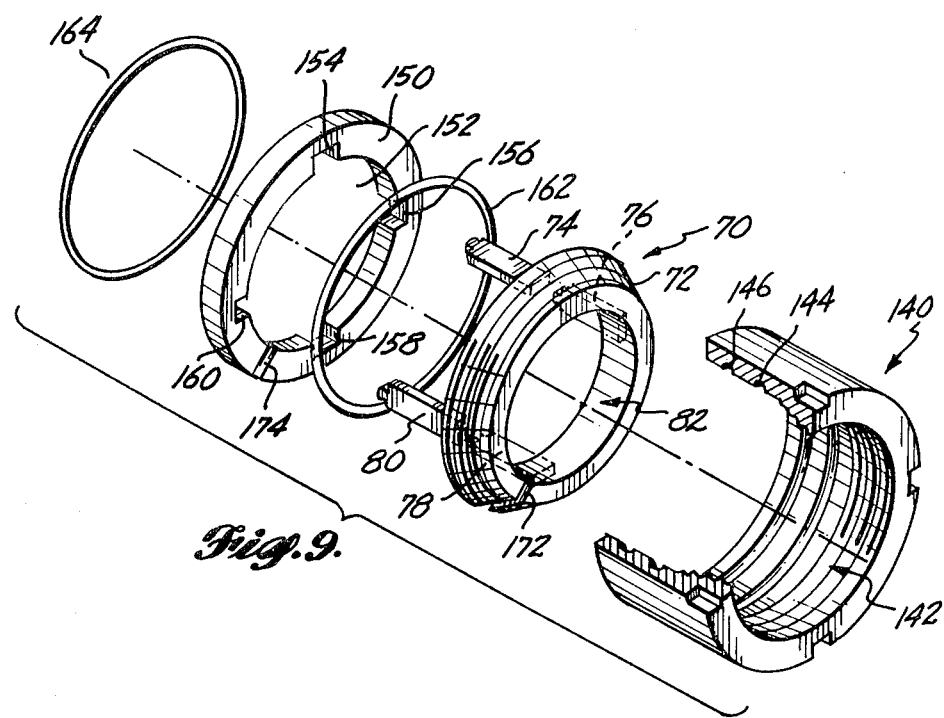
FIG. 9 is an exploded, pictorial view of the components of the pressure arm member in FIG. 7.

Referring now specifically to FIGS. 7 and 9, it will be seen that the periphery of collar 72 of member 70 is theaded and is inwardly tapered in a direction away from pressure arms 74, 76, 78, and 80. A contraction nut 140 has a generally cylindrical shape and includes a central aperture 142 that is defined in part by an inwardly tapering, threaded surface that is complementary to the inward taper of the periphery of collar 72. The inner surface of contraction nut 140 defining central aperture 142 is also provided with spaced-apart, circumferential grooves 144 and 146. A spacer ring 150 has an outer diameter that is substantially equal to the diameter of central aperture 142 between grooves 144 and 146 and includes a central aperture 152 that is defined in part by four orthogonally spaced notches 154, 156, 158, and 160. O-rings 162 and 164 are also provided whose diameters are generally complementary to those of grooves 144 and 146.

In assembly, collar 72 of member 70 is threaded into contraction nut 140 and spacer ring 150 is maintained in place between grooves 144 and 146 by O-rings 162 and 164, that respectively fit into grooves 144 and 146. Upon assembly, it will be noted that pressure arms 74, 76, 78, and 80 fit within notches 154, 156, 158, and 160, but are separated therefrom. Alignment of member 70 and spacer ring 150 is achieved by manipulation of two corresponding radial slots 172 and 174 formed in collar 72 and spacer ring 150, respectively. The assembly is then fitted over tool holder 90 and pressed toward the front face of receptacle module 60 until the free ends of pressure arms 74, 76, 78, and 80 engage respective membranes 62, 64, 66, and 68 as previously described. Rotation of contraction nut 140 then compresses collar 72 about tool holder 90 and the free end of contraction nut 140 is received within annular groove 104 formed in the front face of cylindrical member 96 of receptacle module 60.

To this point, the sensor has been described in terms of being responsive to transverse, axial, and angular displacements. That the sensor also measures transverse force, axial force, and torque can be seen from the following discussion in which specific reference is made to FIG. 10, which shows a schematic representation of the sensor previously described in assembly with a machine tool in which a tool 180 has been inserted into the tool holder.

Figure 10:
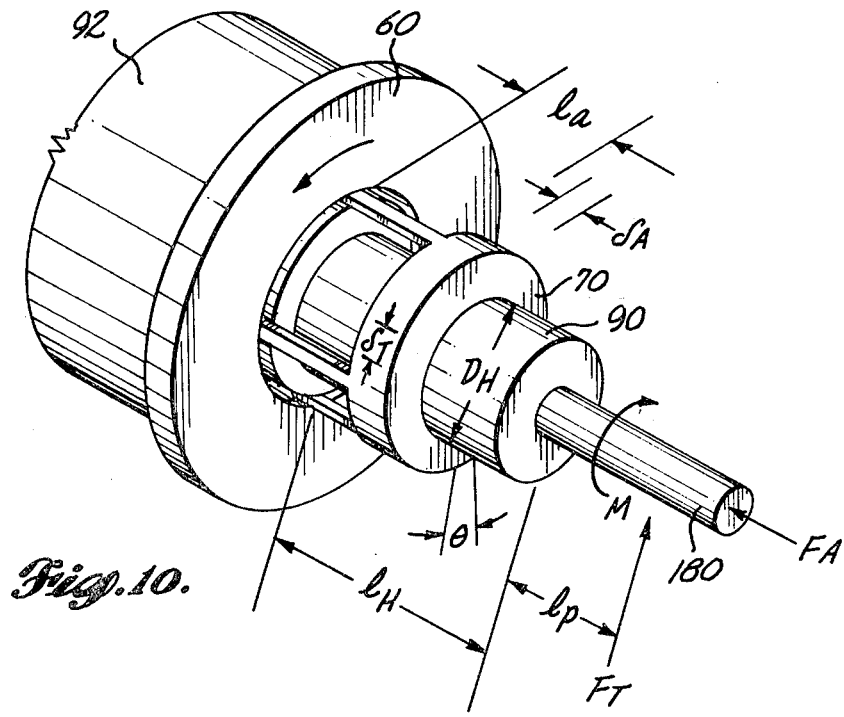
FIG. 10 is a pictorial view illustrating the sensor of FIG. 7 in assembly with a spindle, tool holder and tool.

The relationship between transverse force $F_T$ and transverse displacement $\delta_T$ of member 70 is:

$$\delta_T = \frac{F_T}{EI_H} \left[ \frac{1_H^3 - (1_H - 1_a)^3}{3} + \frac{1_p(1_H^2 - (1_H - 1_a)^2)}{2} \right] \quad (32)$$

where:
$I_H$ = cross-sectional inertia of tool holder $90 = (\pi/64)(D_H)^4$, $D_H$, $I_H$, $1_a$, and $1_p$ are as indicated in FIG. 10.

Assuming that: $E = 29 \times 10^6$ lb/in$^2$; $D_H = 2''$; $1_p = 1''$; $1_H = 2''$ and $1_a = 1''$, it will be seen that relation (32) reduces to:

$$\delta_T = 0.142 \times 10^{-6} F_T \quad (33)$$

where:
$\delta_T$ is in inches,
$F_T$ is in lbs.

For a transverse force $F_T$ of one lb, the transverse displacement $\delta_T$ is accordingly 0.142 microinch. Therefore, the transverse displacement sensitivity $K_{\delta TFT}$ is:

$$K_{\delta TFT} = .142 \text{ microinch per lb} \quad (34)$$

$$= 1 \text{ microinch per 7 lbs} \quad (35)$$

If it is now assumed that the length and cross-sectional area of each pressure arm and the area of each membrane are substantially the same as those set forth in the specific example discussed in conjunction with FIG. 2, it will be remembered that the pressure sensitivity of each pressure chamber to transverse displacement is:

$$PS_{\delta T} = 0.48 \text{ psi per microinch} \quad (36)$$

By equating relations (35) and (36), it can be seen that the pressure sensitivity to transverse force for each pressure chamber is:

$$K_{p\delta T} = .48 \text{ psi per 7 lbs} \quad (37)$$

$$= .07 \text{ psi per lb} \quad (38)$$

Because there are four pressure chambers and pressure transducers responsive to any transverse displacement along sensor axis $x_s$ and along sensor axis $y_s$, the cumulative output signal sensitivity from the four pressure transducers is:

$$K_{vFT} = 0.28 \, K_{tp} \text{ volts per lb} \quad (39)$$

The relationship between torque M and angular displacement $\theta$ of member 70 is:

$$\theta = \frac{32MI_a}{\pi D_H^4 G} \quad (40)$$

where: G = shear modulus of elasticity (for steel, $11 \times 10^6$ lb/in$^2$).

With the assumptions previously made in conjunction with transverse displacement, it will be seen that relation (40) reduces to:

$$\theta = 0.0579 \times 10^{-6} M \quad (41)$$

where:
$\theta$ is in radians,
M is in in-lbs.

For a torque M of one in-lb, the angular displacement $\theta$ is accordingly 0.0579 microradian. Therefore, the angular displacement sensitivity $K_{\theta M}$ is:

$$K_{\theta M} = .0579 \text{ microradian per in-lb} \quad (42)$$

$$= 1 \text{ microradian per 17 in-lbs} \quad (43)$$

If it is now assumed that the length and cross-sectional area of each pressure arm and the area of each membrane are substantially the same as those set forth in the specific example discussed in conjunction with FIG. 3, it will be remembered that the pressure sensitivity of each pressure chamber to angular displacements is:

$$PS_\theta = 0.603 \text{ psi per microradian} \quad (44)$$

By equating relations (43) and (44), it can be seen that the pressure sensitivity to torque for each pressure chamber is:

$$K_{pM} = .603 \text{ psi per 17 in-lbs} \quad (45)$$

$$= .035 \text{ psi per in-lb} \quad (46)$$

Because there are eight pressure chambers and pressure transducers responsive to any angular displacement, the cumulative output signal sensitivity from the pressure transducers is:

$$K_{vM} = 0.28 \, K_{\theta p} \text{ volts per in-lb} \quad (47)$$

The relationship between axial force $F_A$ and axial displacement $\delta_A$ of member 70 is:

$$\delta_A = \frac{4F_A 1_a E}{\pi D_H^2} \quad (48)$$

With the assumptions previously made in conjunction with transverse displacement, it will be seen that relation (48) reduces to:

$$\delta_A = 0.011 \times 10^6 F_A \quad (49)$$

where:

$\delta_A$ is in inches,
$F_A$ is in lbs.

For an axial force $F_A$ of one lb, the axial displacement $\delta_A$ is accordingly 0.011 microinch. Therefore, the axial displacement sensitivity $K_{\delta AFA}$ is:

$$K_{\delta AFA} = .011 \text{ microinch per lb} \tag{50}$$

$$= 1 \text{ microinch per 91 lbs} \tag{51}$$

If it is now assumed that the length and cross-sectional area of each pressure arm and the area and rigidity of each membrane are the same as those set forth in the specific example discussed in conjunction with FIG. 4, it will be remembered that the pressure sensitivity of each pressure chamber to axial displacements is:

$$PS_{67A} = 2.86 \text{ psi per microinch} \tag{52}$$

By equating relations (51) and (52), it can be seen that the pressure sensitivity to axial force for each pressure chamber is:

$$K_{pFA} = 2.86 \text{ psi per 91 lbs} \tag{53}$$

$$= .031 \text{ psi per lb} \tag{54}$$

Because there are eight pressure chambers and pressure transducers responsive to any axial displacement, the cumulative output signal sensitivity from the pressure transducers is:

$$K_{vFA} = 0.25 \, K_{zp} \text{ volts per lb} \tag{55}$$

Figure 11:
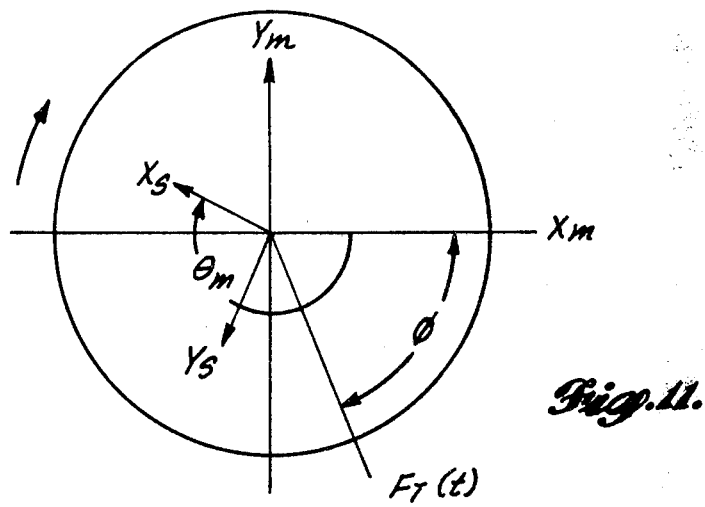
FIG. 11 is a schematic representation of the various axes of the machine tool and of the sensor in FIG. 10.
Figure 12:
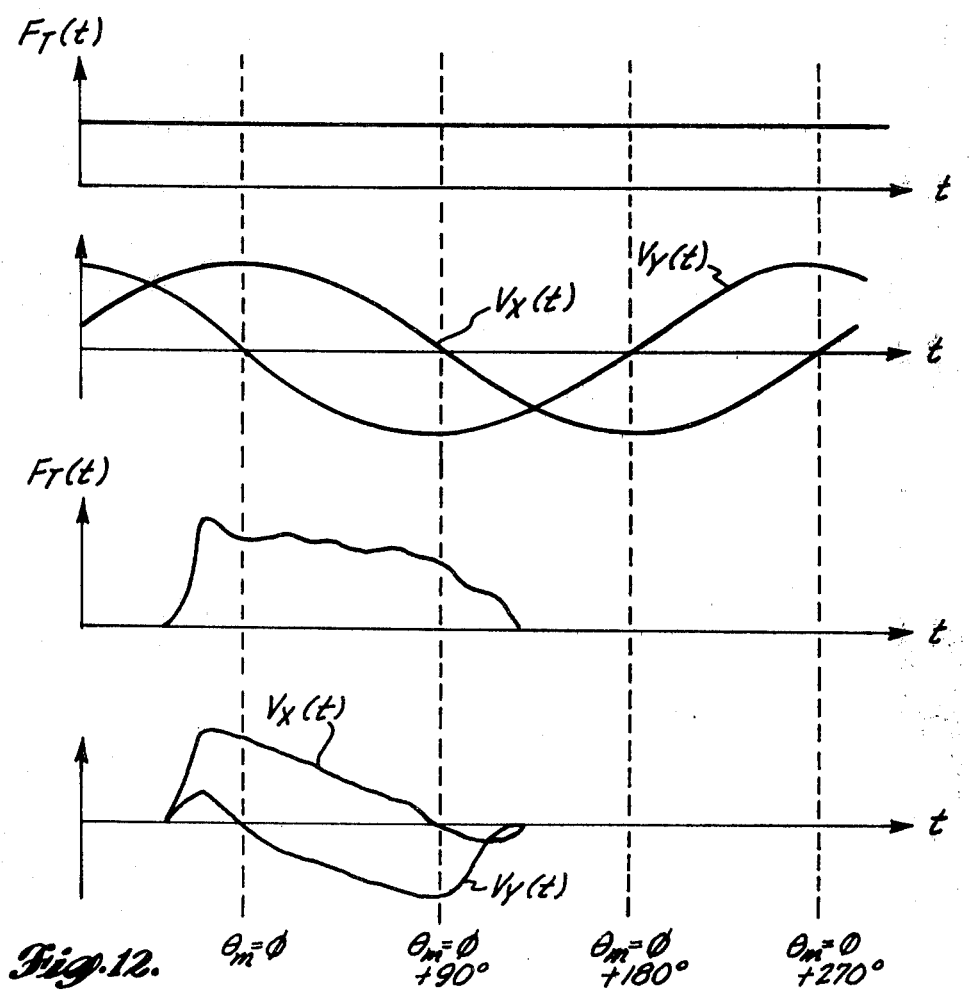
FIG. 12 is a set of wave form diagrams illustrating the variation in force measured by the sensor along orthogonal sensor axes with rotation of the spindle.

Referring now to FIGS. 11 and 12, it will be seen that the angle $\phi$ of the transverse force $F_T$ relative to one of the machine axes (e.g., machine axis $x_m$) may be determined by measuring the angle $\theta_m$ between one of the sensor axes (e.g., sensor axis $x_s$) and that machine axis and by monitoring the output signals from the pressure transducers representing transverse displacements along the sensor axes $x_s$ and $y_s$ during revolution of the spindle. As previously described, angle $\theta_m$ is measured by an angular position sensor such as encoded member 130 and source and detector 132 (FIG. 7). Let it be assumed that the cumulative output signal from the pressure transducers in response to transverse displacements along sensor axis $x_s$ is $V_x(t)$, that the cumulative output signal from the pressure transducers in response to transverse displacements along sensor axis $y_s$ is $V_y(t)$, and that a transverse force $F_T(t)$ is exerted on the tool at a constant angle $\phi$ with (a) a constant value and (b) a time-varying value.

Considering now the situation in which $F_T(t)$ has a constant value, it will be seen from FIG. 12 that $V_x(t)$ and $V_y(t)$ each undergo a substantially sinusoidal variation upon a 360° revolution of the spindle and that $V_y(t)$ is shifted in phase from $V_x(t)$ by 90°. There are, however, four times during the revolution of the spindle when one of $V_x(t)$ and $V_y(t)$ is zero and the other is nonzero. As indicated in FIG. 12, these times occur when sensor axis $x_s$ is aligned with and shifted by 90°, 180°, and 270° from $F_T(t)$. Since the angle $\theta$ is known at these times (through measurement by the angular position sensor), the angle $\phi$ is also known.

Considering now the situation in which transverse force $F_T(t)$ has a time-varying value, it will be noted that the angle $\phi$ can be determined in the manner previously described provided that the duration of $F_T(t)$ is greater than the time required for the spindle to revolve by 90°.

As an alternative, angle $\phi$ may be determined by use of the following relationship:

$$\phi = \theta_m - \tan^{-1} \frac{V_y(t)}{V_x(t)} \tag{56}$$

As can be seen from a review of relation (32) previously set forth, the transverse displacement $\delta_T$ that results from a transverse force $F_T$ applied to tool 180 varies in relation to the distance $l_p$ between the plane of transverse loading and the front face of tool holder 90. With particular reference to FIG. 13, it will be seen that when tool 180 is advanced in a predetermined FEED direction relative to a workpiece 200, the plane of transverse loading is near the end of tool 180 at the time when tool 180 is just engaging workpiece 200 and the plane of transverse loading moves toward the shank of tool 180 as the machining operation continues. In order to determine the plane of transverse loading during the machining operation, the second embodiment of the sensor illustrated in FIGS. 13, 14, and 15 may be used.

Pressure arm member 70 in the first embodiment of FIGS. 7 through 10 is replaced by an inner pressure arm member 202 and an outer pressure arm member 204, and contraction nut 140 is replaced by a contraction nut 206. Otherwise, the components of the second embodiment are identical to those previously described for the first embodiment. Inner member 202 includes a collar 208 and two diametrically opposed pressure arms 210 and 212 extending therefrom. Likewise, outer member 204 includes a collar 214 and two diametrically opposed pressure arms 216 and 218 extending therefrom. In assembly, collar 208 is threaded into contraction nut 206 and the resultant assembly is then fitted over tool holder 90 until the free ends of pressure arms 210 and 212 come into engagement with diametrically opposed membranes in receptacle module 60. Rotation of contraction nut 206 then compresses collar 208 about tool holder 90. Collar 214 is then fitted over tool holder 90, and is moved toward receptacle module 60 until the free arms of pressure arms 216 and 218 engage diametrically opposed membranes in receptacle module 60. Collar 214 (which is provided with a radial slot 220) is then compressed about tool holder 90 by rotation of a threaded fastener 222. When so assembled, it is to be noted that pressure arms 216 and 218 pass through but are separated from notches 224 in collar 208 and that a support ring and two O-rings (not illustrated) are installed within contraction nut 206 in a manner similar to that previously described for the first embodiment.

The length $l_I$ of each of the inner pressure arms 210 and 212 is less than the length $l_O$ of each of the outer pressure arms 216 and 218. The two pairs of pressure chambers associated with the membranes which are contacted by inner pressure arms 210 and 212 are responsive to transverse displacements along a first sensor axis (e.g., sensor axis $x_s$) referenced to a first plant (that of collar 208), and the two remaining pairs of pressure chambers associated with the membranes which are contacted by outer pressure arms 216 and 218 are responsive to transverse displacements along a second sensor axis (e.g., sensor axis $y_s$) referenced to a second plane (that of collar 214).

By analogy to relation (32), the transverse displacement $\delta_I$ of each inner pressure arm is:

$$\delta_I = \frac{F_T \cos(\theta_m - \phi)}{EI_H} \left[ \frac{l_H^3 - (l_H - l_I)^3}{3} + \frac{l_p(l_H^2 - (l_H - l_I)^2)}{2} \right] \tag{57}$$

where:

$\theta_m$, $\phi$, E and $l_H$ are as previously described,
$F_T$, $l_H$, $l_I$ and $l_p$ are as indicated in FIG. 13.

Likewise, the transverse displacement $\delta_O$ of each outer pressure arm is:

$$\delta_O = \frac{F_T \sin(\theta_m - \phi)}{EI_H} \left[ \frac{l_H^3 - (l_H - l_O)^3}{3} + \frac{l_p(l_H^2 - (l_H - l_O)^2)}{2} \right] \tag{58}$$

where: $l_O$ is as indicated in FIG. 13.

Considering relations (57) and (58) the plane of transverse loading can be determined as follows.

The pressure $P_I$ that is produced in each pressure chamber in response to transverse displacement $\delta_I$ and the pressure $P_O$ that is developed in each pressure chamber in response to transverse displacement $\delta_O$ are:

$$P_I = \frac{3EI_I \delta_I}{A_I l_I^3} \tag{59}$$

$$P_O = \frac{3EI_O \delta_O}{A_O l_O^3} \tag{60}$$

where:

$I_I$ and $I_O$ are the cross-sectional inertias of the inner and outer pressure arms, respectively,
$A_I$ and $A_O$ are the areas of the corresponding membranes for the inner and outer pressure arms, respectively.

By combining relations (57) and (59) and relations (58) and (60), the relations for pressures $P_I$ and $P_O$ can be written as:

$$P_I = F_T \cos(\theta_m - \phi)(a + bl_p) \tag{61}$$

$$P_O = F_T \sin(\theta_m - \phi)(c + dl_p) \tag{62}$$

where: a, b, c and d are constants that characterize the structure of tool holder 90 and each pressure arm.

Dividing relation (62) by relation (61):

$$\frac{P_O}{P_I} = \tan(\theta_m - \phi) \left( \frac{c + dl_p}{a + bl_p} \right) \tag{63}$$

Solving relation (63) for the determined value of distance $l_p$ (or, $l_p^*$):

$$l_p^* = \frac{a\left(\frac{P_O}{P_I}\right) - c \tan(\theta_m - \phi)}{d \tan(\theta_m - \phi) - b\left(\frac{P_O}{P_I}\right)} \tag{64}$$

Therefore, the plane of transverse loading can be determined by measuring the pressures developed in response to transverse displacements along sensor axes $x_s$ and $y_s$, by measuring the angle $\theta_m$, and by determining the angle $\phi$ (reference relation (56)).

As previously discussed in conjunction with FIGS. 11 and 12, an independent determination of the angle $\phi$ is possible only when the duration of the transverse force is greater than the time that it takes for the spindle to revolve by 90°. In practically every machining operation, the transverse force will have a shorter duration only when machining is being carried out with the end of tool 180. In this situation, the value of $l_p^*$ may be assumed to be the flute length FL of tool 180 from its end to its shank. It is also desirable to limit the range of $l_p^*$ to:

$$0 \leq l_p^* \leq FL \tag{65}$$

and to initialize $l_p^*$ to FL before the machining operation commences.

Having thus provided a dynamic determination of the plane of transverse loading, the information that is obtained can be used to modify the pressure measurements made during the machining operation in order to compensate those pressure measurements for variations in the plane of loading. In this regard, let it be assumed that $l_p^*$ is computed at periodic intervals $\tau$ and that each interval $\tau$ is a fixed period of time that is asynchronous with or synchronous with revolution of spindle 92. Let it be further assumed that all pressure measurements during the machining operation are made with an assumed value of $l_p$ for which tool holder 90 has been calibrated. Given these assumptions, the pressure measurements may be modified upon each periodic computation of $l_p^*$ as follows:

$$P_I = P_I(\text{measured}) \left( \frac{a + bl_p^*}{a + bl_p} \text{ (calibrated)} \right) \tag{66}$$

$$P_O = P_O(\text{measured}) \left( \frac{c + dl_p^*}{c + dl_p} \text{ (calibrated)} \right) \tag{67}$$

From relations (66) and (67), it will be seen that the values of $P_I$ and $P_O$ are each increased and decreased in response to respective increases and decreases in the transverse plane of loading from that transverse plane of loading for which tool holder 90 has been calibrated.

Referring now to FIG. 16, a third embodiment of the sensor for use with a machine tool having a stationary tool is illustrated. A tool 230 is mounted on a tool holder 232 that is received within a tool post 234. The sensor includes a receptacle module 236 affixed to tool post 234 and a pressure arm member 238 affixed to tool holder 232.

Receptacle module 236 includes a rectangular block 240 that is mounted on the front face of tool post 234 by a plurality of fasteners 242 and that has defined therein a central, rectangular aperture 244 that is aligned with a corresponding aperture (not illustrated) in tool post 234. A rectangular groove 246 is formed in the front face of block 240 and surrounds aperture 244. At four orthogonally disposed locations in groove 246, recesses extend into block 240 from groove 246 and membranes 248 are mounted in these recesses so that each membrane forms the front wall and one sidewall of each of a pair of pressure chambers. Each pressure chamber is provided with a pressure transducer 250, with the pressure chamber being filled with an incompressible fluid and with the associated pressure transducer 250 being installed through a corresponding port 252 extending into the pressure chamber from a side of block 240.

Pressure arm member 238 includes four rectangular bars 254 and four pressure arms 256, with each pressure arm 256 being integral with and extending normally from one of bars 254. Tool holder 232 has a rectangular cross section, and each bar 254 is disposed on one side of tool holder 232 so that each bar 254 extends transversely to the longitudinal dimension of tool holder 232 and so that the associated pressure arm 256 extends parallel to the longitudinal dimension of tool holder 232. When so disposed, the lower surface of each bar 254 rests on the corresponding side of tool holder 232 and the associated pressure arm 256 is separated therefrom. Pressure arm member 238 also includes four rectangular bars 258. Each rectangular bar 258 includes a groove which receives a corresponding one of rectangular bars 254, and bars 258 are secured to each other by a plurality of fasteners 260 so as to compress bars 254 against the sides of tool holder 232.

When tool holder 232 is installed into tool post 234, tool holder 232 is received within aperture 244 of member 240 and within the corresponding aperture in tool post 234, and the free ends of pressure arms 256 engage corresponding ones of membranes 248. Tool holder 232 is maintained within tool post 234 by a fastener 262 bearing on the portion of tool holder 232 received within the aperture within tool post 234, and fastener 262 also serves to force the free ends of pressure arms 256 against the corresponding ones of membranes 248 so as to preload each of the pressure chambers. From the preceding discussion of the embodiments of the sensor for use with a machine tool having a rotating tool, it will be appreciated that the sensor in FIG. 16 functions to provide output signals from pressure transducers 250 that are a measure of the transverse and axial forces on tool holder 232 along orthogonal sensor axes $x_s$, $y_s$, and $z_s$.

Figure 17:
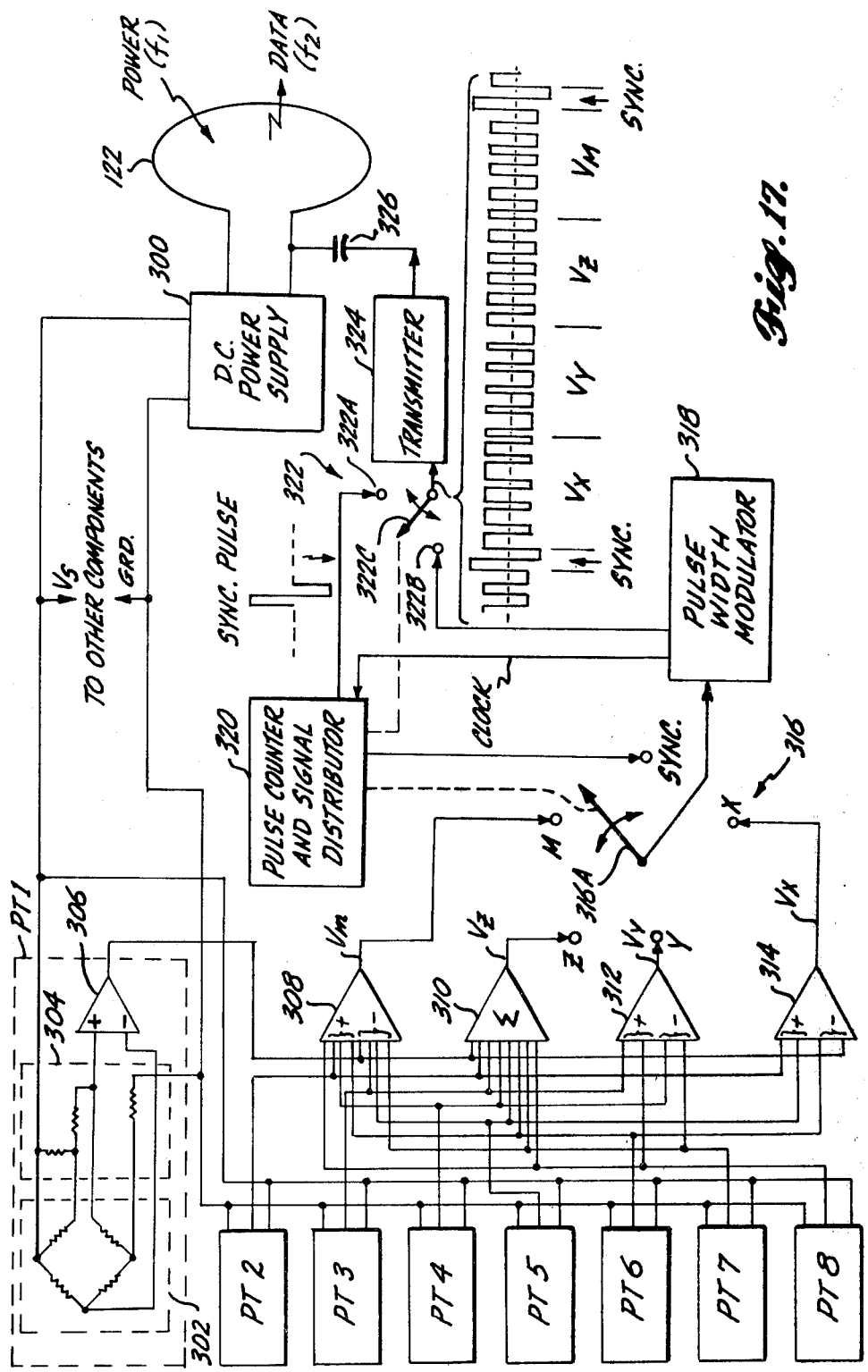
FIG. 17 is an electrical block diagram of the portion of the sensor within the receptacle module.
Figure 18:
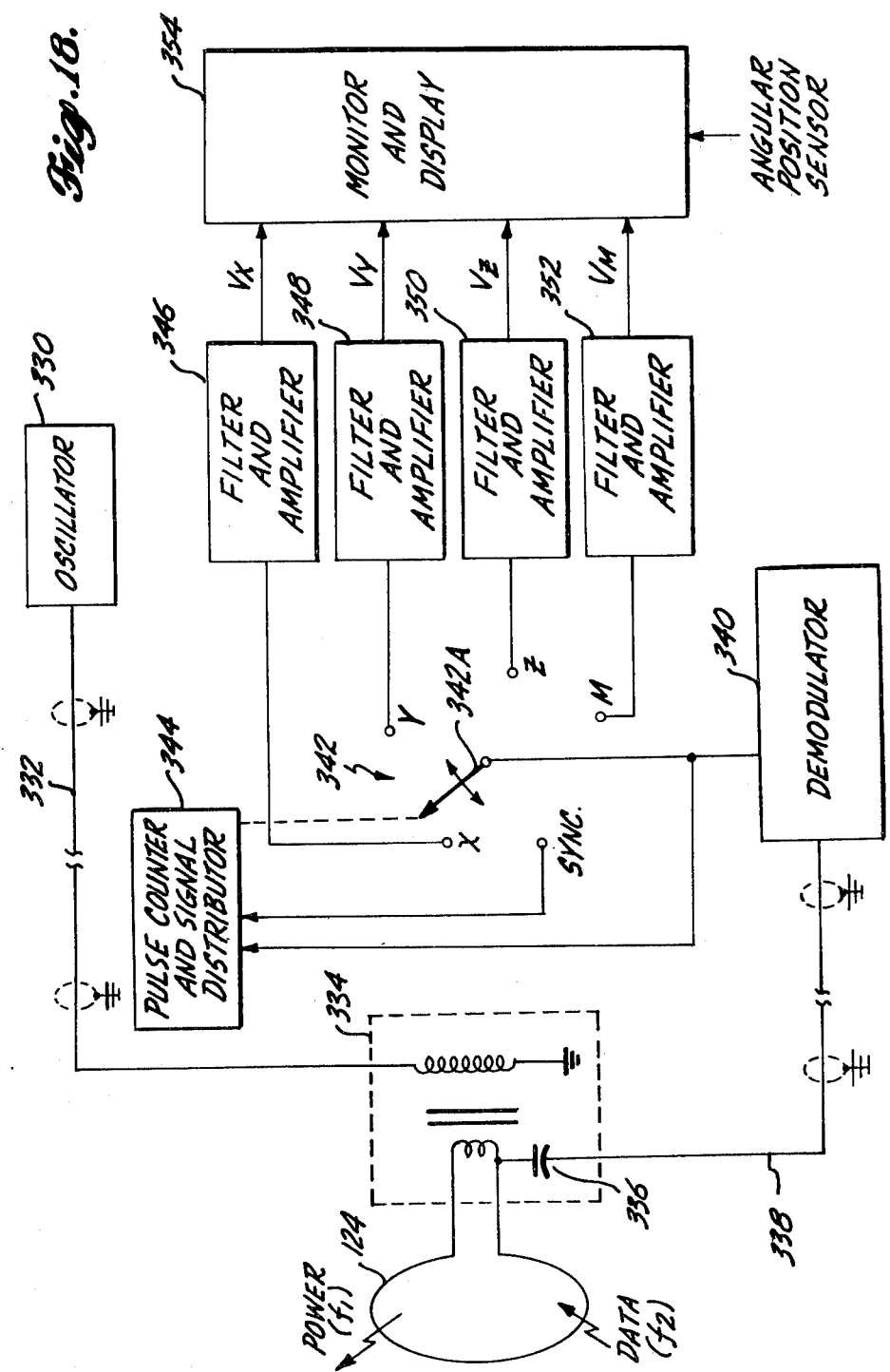
FIG. 18 is an electrical block diagram of the portion of the sensor external to the receptacle module.

Because receptacle module 236 in FIG. 16 is stationary relative to tool post 234 and the remaining portions of the machine tool, the output signals from pressure transducers 250 may be supplied to a desired utilization device by means of electrical leads passing, for example, through a channel 264 formed in the rear face of member 240. Because the receptacle module 60 in the embodiments of the sensor illustrated in FIGS. 7 through 10 and 13 through 15 rotates relative to the machine tool, such a direct electrical connection is not possible and therefore provision must be made for coupling these output signals to the utilization device. With reference now to FIGS. 17 and 18, a preferred embodiment of circuits for combining and coupling the output signals from the pressure transducers in a rotating receptacle module are illustrated. FIG. 17 depicts the circuit that is contained within receptacle module 60, and FIG. 18 depicts the circuit that is external to receptacle module 60 and that is at a stationary location.

Referring now to FIG. 17, loop antenna 122 in receptacle module 60 receives a POWER signal that comprises an RF signal at a predetermined frequency $f_1$ (e.g., 160 kHz) which is transmitted by stationary loop 124. The POWER signal is applied to the input of a DC power supply 300 which develops from the POWER signal a DC supply voltage $V_S$ (e.g., 8 vdc). This DC supply voltage is coupled by appropriate leads to each of pressure transducers PT1 ... PT8 and to the remaining components of the circuit illustrated in FIG. 17 (all of which are contained within receptacle module 60 as previously described). Each of the pressure transducers includes a strain gauge bridge circuit 302, a compensation circuit 304, and an operational amplifier 306 whose output signal is proportional to the pressure within the corresponding pressure chamber. The pressure transducer output signals are connected by appropriate leads to the inputs of amplifiers 308, 310, 312, and 314.

The output signals from pressure transducers PT2, PT4, PT6, and PT8 are summed at a noninverting input of amplifier 308 and the output signals from pressure transducers PT1, PT3, PT5, and PT7 are summed at an inverting input of amplifier 308, whereby an output signal $V_M$ from amplifier 308 is proportional to measured torque (or angular displacement). The output signals from pressure transducers PT1 ... PT8 are summed at the input to amplifier 310, whereby an output signal $V_Z$ from amplifier 310 is proportional to measured axial force (or axial displacement). The output signals from pressure transducers PT3 and PT8 are summed at a noninverting input of amplifier 312 and the output signals from pressure transducers PT4 and PT7 are summed at an inverting input of amplifier 312, whereby an output signal $V_Y$ from amplifier 312 is proportional to measured transverse force (or transverse displacement) along sensor axis $y_s$. The output signals from pressure transducers PT2 and PT5 are summed at a noninverting input of amplifier 314 and the output signals from pressure transducers PT1 and PT6 are summed at an inverting input of amplifier 314, whereby an output signal $V_X$ from amplifier 314 is proportional to measured transverse force (or transverse displacement) along sensor axis $x_s$.

Output signals $V_m$, $V_y$, and $V_x$ are supplied to respective M, Z, Y, and X stationary contacts of a switch 316 (which may be a semiconductor switch). Switch 316 also includes a SYNC stationary contact and a movable contact 316A adapted to contact each of the stationary contacts in succession. Movable contact 316A is coupled to the input of a pulse width modulator 318 and is controlled by a pulse counter and signal distributor 320. Modulator 318 provides CLOCK pulses to pulse counter and signal distributor 320 at a predetermined frequency which cause pulse counter and signal distributor 320 to provide a periodic SYNC pulse to the SYNC stationary contact of switch 316 and to a first stationary contact of a switch 322 (which may also comprise a semiconductor switch). At the time of each SYNC pulse, pulse counter and signal distributor 320 causes movable contact 316A of switch 316 to engage the SYNC stationary contact thereof, and between successive SYNC pulses, pulse counter and signal distributor 320 causes movable contact 316A of switch 316 to successively engage the X, Y, Z, and M stationary contacts thereof. As a result, the SYNC pulse and output signals $V_X$, $V_Y$, $V_Z$, and $V_M$ are time-multiplexed and successively applied to the input of modulator 318. Each SYNC pulse so supplied resets modulator 318 so that modulator 318 thereafter converts each of output signals $V_X$, $V_Y$, $V_Z$, and $V_M$ into a corresponding train of pulses at a predetermined frequency (e.g., 5 kHz) whose pulse width represents the magnitude of the corresponding output signal. These pulse trains are supplied as a pulse-width-modulated signal from modulator 318 to a second stationary contact 322B of switch 322. Switch 322 includes a movable content 322C which is controlled by pulse counter and signal distributor 320 so as to engage stationary contact 322A when the SYNC pulse is being provided and to engage stationary contact 322B at all other times. Accordingly, the signal on movable contact 322C is the pulse-width-modulated signal from modulator 318 with the SYNC pulses inserted therein. This signal is supplied to the input of a transmitter 324 that includes an oscillator providing an RF carrier signal at a predetermined frequency $f_2$ (which is different from frequency $f_1$) and a modulator that modulates the pulse-width-modulated signal onto the RF carrier signal. The output from transmitter 324 is coupled by a capacitor 326 to loop antenna 122, whereupon loop antenna 122 transmits a DATA signal comprising the RF carrier signal at frequency $f_2$ modulated with the pulse-width-modulated signal.

Referring now to FIG. 18, the circuit therein includes an oscillator 330 which provides an RF output signal at frequency $f_1$. This RF output signal is coupled by a shielded cable 332 to the primary of a transformer 334 whose secondary is coupled to loop antenna 124, thereby resulting in the transmission of the POWER signal by loop antenna 124. The DATA signal is received by loop antenna 124 and coupled through a capacitor 336 connected to the secondary of transformer 334 and through a shielded cable 338 to the input of a demodulator 340. Demodulator 340 removes the pulse-width-modulated signal from the RF carrier signal (at frequency $f_2$) and supplies the pulse-width-modulated signal to a movable content 342A of a switch 342 (which may comprise a semiconductor switch) and to a first input of a pulse counter and signal distributor 344. Switch 342 also includes SYNC, X, Y, Z, and M stationary contacts. The SYNC stationary contact is connected to a second input of pulse counter and signal distributor 344, and the X, Y, Z, and M stationary contacts are coupled to inputs of respective filter and amplifier circuits 346, 348, 350, and 352. Pulse counter and signal distributor 344 is clocked by the pulse-width-modulated signal supplied to its first input so as to cause movable contact 342A of switch 342 to successively engage the SYNC, X, Y, Z, and M stationary contacts thereof. The operation of pulse counter and signal distributor 344 in so moving movable contact 342A is synchronized by the SYNC pulse applied to its second input, so that the pulse trains representing output signals $V_x$, $V_y$, $V_z$, and $V_m$ are demultiplexed and applied in succession to the inputs of circuits 346, 348, 350, and 352. Each of these circuits functions to convert the pulse train supplied thereto into the corresponding output signal, and output signals $V_x$, $V_y$, $V_z$, and $V_m$ are then supplied to the inputs of a monitor and display 354 or to another utilization device as required.

The utilization device such as monitor and display 354 also receives an angular position signal from the angular position sensor such as encoded member 130 and source and detector 132 (FIG. 7). Preferably, the utilization device includes a microprocessor that is programmed in a conventional manner to convert signal $V_x$ into measured values of transverse force along sensor axis $x_s$, to convert signal $V_y$ into measured values of tranverse force along sensor axis $y_s$, to convert signal $V_z$ into measured values of axial force along sensor axis $z_s$, to convert signal $V_m$ into measured values of torque about sensor axis $z_s$, to determine a value of the angle $\phi$ of transverse force relative to machine axis $x_m$, to determine a value of the distance $l_p^*$ representing the plane of transverse loading, and to compensate the measured values of transverse force along sensor axes $x_s$ and $y_s$ for variations in the plane of loading, all as previously described.

The embodiments of the sensor previously described are particularly adapted for retrofit of existing machine tools of a particular type without substantial modification to the machine tool structure. Those skilled in the art will appreciate that the structure of the sensor may be modified in order to retrofit other types of existing machine tools. For example, the tool holder in some types of machine tools having a rotating tool is face-mounted to the spindle or driven by drive keys that are mounted in the spindle face. Since the receptacle module in this situation cannot be mounted on the spindle face, the receptacle module may be clamped about the periphery of the spindle and appropriate modifications may be made to the remaining components of the sensor including the pressure arm member.

Embodiments of the sensor whose components are an integral part of a machine tool are illustrated in FIGS. 19 and 20. In FIG. 19, the machine tool has a rotating spindle 400 on whose face is mounted a receptacle module 402. Receptacle module 402 is substantially identical in configuration to receptacle module 60 previously described, but is mounted to the face of spindle 400 so that the various membranes therein are positioned adjacent the face of spindle 400 (e.g., the position of receptacle module 402 with respect to spindle 400 in FIG. 19 is reversed from the position of receptacle module 60 with respect to spindle 92 in FIG. 7). Spindle 400 is provided with four orthogonally disposed bores 404 that extend into spindle 400 from its face. Bores 404 are parallel to each other and are each parallel to the longitudinal axis of spindle 400. A cylindrical pressure arm 406 is contained within each bore 404, with each pressure arm 406 having a first end 408 that engages the inner end of its corresponding bore 404 with a locking taper fit that is maintained by an adhesive material (such as epoxy). From its end 408, each pressure arm 406 is separated from the remainder of its corresponding bore 404 and terminates in a second end 410 that projects beyond the face of spindle 400 and that engages one of the membranes in receptacle module 402.

From relation (32) previously discussed, it will be seen that the transverse displacement $\delta_T$ of each pressure arm in the sensor embodiments previously discussed in response to transverse force $F_T$ is dependent on the length of the tool holder, the length of the pressure arm, the distance between the face of the tool holder and the plane of transverse loading, and the cross-sectional inertia of the tool holder. Likewise, the transverse displacement $\delta_T$ of each pressure arm 404 in the sensor embodiment in FIG. 19 in response to transverse force $F_T$ is dependent on the length of a tool holder that is inserted into spindle 400, the length of the pressure arm, the distance between the face of the tool holder and the plane of transverse loading, and the cross-sectional inertia of spindle 400.

Specifically, $$\delta_T = \frac{F_T}{EI_{spdl}} \left[ \frac{l_a^3}{3} + \frac{(l_H + l_p)(l_a^2)}{2} \right] \tag{68}$$

where:

E=Young's Modulus,
$I_{spdl}$=Cross-sectional inertia of spindle $400 = (\pi/64)(D_{spdl})^4$,
$D_{spdl}$=diameter of spindle 400,
$l_a$=length of each pressure arm 406,
$l_H$=length of the tool holder
$l_p$=distance from the plane of transverse loading to the face of the tool holder To give a specific example, let is be assumed that: each pressure arm is of steel; $D_{spdl}=6''$; $l_a=6''$; $l_H=3''$; and, $l_p=3''$. Substituting these values in relation (68) it can be seen that:

$$\delta_T = 0.1 \times 10^{-6} F_T \tag{69}$$

where:
$\delta_T$ is in inches,
$F_T$ is in lbs.

For a transverse force $F_T$ of one lb, the transverse displacement $\delta_T$ is accordingly 0.1 microinch. Therefore, the transverse displacement sensitivity is:

$$K_{\delta TFT} = .1 \text{ microinch per lb} \tag{70}$$

$$= 1 \text{ microinch per 10 lbs} \tag{71}$$

From relation (1), it will be seen that the force $F_{mem}$ on the membrane of a single pressure chamber in response to a transverse displacement $\delta_T$ is related to the transverse rigidity of the pressure arm. In the specific example being discussed, let it be further assumed that each pressure arm 406 has a diameter (D) of 1''. Substituting the values in the specific example into relation (1), $$F_{mem} = \frac{3(29 \times 10^6)\left(\frac{\pi}{64}\right)(1)^4(\delta_T)}{(6)^3} \tag{72}$$

$$= 2.0 \times 10^4(\delta_T) \tag{73}$$

where: $2.0 \times 10^4$ is the transverse rigidity $R_{transverse}$ in lb/in.

From relation (4), it will be seen that the pressure $P_{mem}$ in a single pressure chamber is proportional to the ratio of force $F_{mem}$ and the area $A_{mem}$ of the pressure chamber membrane. In the specific example being discussed, let it be further assumed that the membrane of each pressure chamber within receptacle module 402 has the same area as the membranes previously discussed ($3/16'' \times 3/16''$). From relations (4) and (73), the pressure $P_{mem}$ in a single pressure chamber in response to a transverse displacement of one microinch is:

$$P_{mem} = \frac{2.0 \times 10^4(1 \times 10^{-6})}{\left(\frac{3}{16}\right)^2} \tag{74}$$

$$= .57 \text{ psi} \tag{75}$$

Therefore, each pressure chamber has a pressure sensitivity to transverse displacements of $$PS_{\delta T} = 0.57 \text{ psi per microinch} \tag{76}$$

By equating relations (71) and (76), it can be seen that each pressure chamber has a pressure sensitivity to transverse force:

$$K_{p\delta T} = 0.06 \text{ psi per lb} \tag{77}$$

which is substantially equivalent to the corresponding pressure sensitivity of the tool holder sensor embodiment previously discussed (see relation (38)).

Similar analyses can be made to demonstrate that the pressure sensitivities of the sensor embodiment in FIG. 19 to axial displacements (and axial forces) and to angular displacements (and torques) are substantially equivalent to those of the sensor embodiments previously discussed.

In FIG. 20, a machine tool having a stationary tool includes a tool post 500 on whose face is mounted a receptacle module 502. Receptacle module 502 is substantially identical to receptacle module 236 in FIG. 16 but is positioned so that the membranes therein are positioned adjacent the face of tool post 500. In a manner identical to the sensor embodiment in FIG. 19, tool post 500 is provided with four orthogonally spaced bores 504 that extend into tool post 500 from the front face thereof. A pressure arm 506 is located within each of bores 504 so that a first end thereof engages the end of its corresponding bore 504 with a locking taper fit and so that a second end thereof projects beyond the face of tool post 500 and engages a corresponding one of the membranes in receptacle module 502.

In certain situations, one or more of pressure arms 506 may be located so as to interfere with a fastener that mounts the tool holder to the tool post, such as fastener 508. In these situations, one of the pressure arms (and corresponding membranes and pressure chambers) may be eliminated from each sensor axis since the invention requires only two orthogonally disposed pressure arms, membranes and pressure chambers for sensing transverse forces (and displacements) and axial forces (and displacements).

While the invention has been described with reference to several embodiments, it is to be clearly understood by those skilled in the art that the invention is not limited thereto and that the scope of the invention is to be interpreted only in conjunction with the appended claims.

The embodiments of the invention in which an exclusive property or privilege is claimed are defined as follows:

1. A sensor for use with a machine tool in which substantially all of the load on a first machine tool member is borne by a second machine tool member, said sensor being responsive to displacement of the first machine tool member to measure the force and torque exerted thereon and comprising:

first means adapted to be mounted in proximity to the first machine tool member, said first means including: a first pressure chamber that is filled with an incompressible fluid; a membrane of a rigid material that forms at least one wall of said first pressure chamber; and, means measuring the pressure within said first pressure chamber;

an elongated pressure arm of a rigid material; and, means for affixing a first end of said pressure arm to the first machine tool member at a location along the longitudinal axis thereof at which force and torque are to be measured so that a second end of said pressure arm bears on said membrane in said first means.

2. The sensor of claim 1, wherein the second machine tool member is disposed at a second location along said longitudinal axis of the first machine tool member and wherein said first means includes means for affixing said first means to the second machine tool member.

3. The sensor of claim 2, wherein the first machine tool member is a tool holder and the second machine tool member is a rotatable spindle to which the tool holder is mounted and with which the tool holder rotates.

4. The sensor of claim 2, wherein the first machine tool member is a tool holder and the second machine tool member is a nonrotatable tool post to which the tool holder is mounted and relative to which the tool holder is stationary.

5. The sensor of claim 1, wherein said first means includes means for affixing said first means to the first machine tool member at a second location along said longitudinal axis thereof.

6. The sensor of claim 5, wherein the first machine tool member is a rotatable spindle.

7. The sensor of claim 5, wherein the first machine tool member is a tool post.

8. The sensor of claim 1, wherein said pressure arm extends substantially parallel to said longitudinal axis of the first machine tool member.

9. The sensor of claim 8, wherein said membrane extends transversely to said longitudinal axis when said first means is mounted, and wherein said second end of said pressure arm is provided with a portion that bears normally on said membrane, whereby the pressure within said first pressure chamber is related to axial force exerted on and effecting axial displacement of the first machine tool member.

10. The sensor of claim 8, wherein said membrane extends parallel to said longitudinal axis when said first means is mounted, and wherein said second end of said pressure arm is provided with a portion that bears normally on said membrane, whereby the pressure within said first pressure chamber is related to transverse force and torque exerted on and effecting transverse displacement and angular displacement of the first machine tool member.

11. The sensor of claim 8, wherein said membrane includes a first portion forming a first wall of said first pressure chamber and a second portion extending normally to said first portion and forming a second wall of said first pressure chamber; where said first portion of said membrane extends transversely to said longitudinal axis and said second portion of said membrane extends parallel to said longitudinal axis when said first means is mounted; and, wherein said second end of said pressure arm is provided with a first portion that bears normally on said first portion of said membrane and a second portion that bears normally on said second portion of said membrane, whereby the pressure within said first pressure chamber is related to axial force, transverse force, and torque exerted on and effecting axial displacement, transverse displacement and angular displacement of the first machine tool member.

12. The sensor of claim 1, wherein: said first means includes a second pressure chamber that is proximate to said first pressure chamber; said membrane includes one portion that forms at least one wall of said first pressure chamber and another portion that forms at least one wall of said second pressure chamber; said first means includes means measuring the pressure within said second pressure chamber; and, said second end of said pressure arm bears on both portions of said membrane in said first means.

13. The sensor of claim 12, wherein said pressure arm extends substantially parallel to said longitudinal axis of the first machine tool member.

14. The sensor of claim 12, wherein said membrane includes a first portion forming a first wall of said first pressure chamber, a second portion extending normally to said first portion and forming a second wall of said first pressure chamber, a third portion forming a first wall of said second pressure chamber, and a fourth portion extending normally to said third portion and forming a second wall of said second pressure chamber; wherein said first and third portions of said membrane extend transversely to said longitudinal axis and said second and fourth portions of said membrane extend parallel to said longitudinal axis when said first means is mounted; and, wherein said second end of said pressure arm is provided with first, second, third, and fourth portions that bear normally on said first, second, third, and fourth portions of said membrane, respectively, whereby the pressure within each of said first and second pressure chambers is related to axial force, transverse force and torque exerted on and effecting axial displacement, transverse displacement and angular displacement of the first machine tool member.

15. The sensor of claim 14, wherein said first and third portions of said membrane are substantially coplanar whereby the pressures within said first and second pressure chambers are related to the same components of axial force effecting axial displacement.

16. The sensor of claim 14, wherein said second and fourth portions of said membrane are parallel to each other, whereby the pressures within said first and second pressure chambers are related to the same components of transverse force and torque effecting transverse displacement and angular displacement.

17. The sensor of claim 12, wherein said means measuring the pressure within said first pressure chamber and said means measuring the pressure within said second pressure chamber are each a pressure transducer that provides an electrical output signal related to the pressure within the corresponding pressure chamber.

18. The sensor of claim 1, wherein said means measuring the pressure within said first pressure chamber is a pressure transducer that provides an electrical output signal related to the pressure within said first pressure chamber.

19. The sensor of claim 1, wherein the rigidity of said membrane is less than ten percent of the rigidity of said pressure arm.

20. A sensor for use with a machine tool in which substantially all of the load on a first machine tool member is borne by a second machine tool member, said sensor being responsive to displacement of the first machine tool member to measure the force and torque exerted thereon and comprising:

first means mounted in proximity to the first machine tool member, said first means including: a plurality of pressure chambers, each of which is filled with an incompressible fluid, said pressure chambers being disposed in pairs that are orthogonally disposed about the longitudinal axis of the first machine tool member; a plurality of membranes corresponding in number to said pairs of pressure chambers, each of said membranes being composed of a rigid material and each forming at least one wall of each of the pressure chambers within one of said pairs thereof; and, means measuring the pressure within each of said pressure chambers;

a plurality of elongated pressure arms corresponding in number to said membranes and each being composed of a rigid material; and, second means affixing a first end of each of said pressure arms to the first machine tool member at a location along said longitudinal axis thereof at which force and torque are to be measured so that a second end of each of said pressure arms bears on a corresponding one of said membranes in said first means.

21. The sensor of claim 20, wherein the first machine tool member is a tool holder and the second machine tool member is a spindle of the machine tool, the tool holder being mounted to and rotatable with the spindle; wherein said first means includes means affixing said first means to the spindle so that said membranes face the tool holder; and wherein said second means includes collar means secured to said first ends of said pressure arms and means compressing said collar means about the periphery of the tool holder so that said pressure arms are disposed about the periphery of the tool holder.

22. The sensor of claim 21, wherein said pressure arms have the same length.

23. The sensor of claim 22, wherein said collar means includes a collar that is integral with said pressure arms.

24. The sensor of claim 21, wherein: said pairs of pressure chambers are divided into first and second sets; said pairs of pressure chambers in said first set are located at separated points along a first sensor axis that is transverse to the axis of rotation of the spindle; said pairs of pressure chambers in said second set are located at separated points along a second sensor axis that is transverse to said axis of rotation and that is angularly disposed about said axis of rotation from said first sensor axis; said pressure arms are divided into first and second sets; each pressure arm in said first set has a first length; each pressure arm in said second set has a second length which is different from said first length; said collar means includes a first collar that is integral with the pressure arms in said first set and a second collar that is integral with the pressure arms in said second set; and, said pressure arms in said first set are disposed so that said second ends thereof bear on corresponding membranes of those of said pairs of pressure chambers in said first set and said pressure arms in said second set are disposed so that said second ends thereof bear on corresponding membranes of those of said pairs of pressure chambers in said second set.

25. The sensor of claim 20, wherein the first machine tool member is a rotatable spindle of the machine tool; wherein said first means includes means for affixing said first means to the spindle so that said membranes face the spindle; wherein the spindle is provided with a plurality of elongated bores corresponding in number to said pressure arms and each extending substantially parallel to the axis of rotation of the spindle; wherein said pressure arms are disposed within corresponding ones of said bores so that second ends thereof project beyond the spindle; and, wherein said second means includes means for securing said first end of each of said pressure arms in the corresponding one of said bores.

26. The sensor of claim 20, wherein the second machine tool member is a spindle of the machine tool and the first machine tool member is a member that is mounted to and rotates with the spindle; wherein said first means includes means for mounting said first means to the spindle; and wherein said pairs of pressure chambers, said membranes and said pressure arms are arranged and disposed so that the pressures within said pressure chambers are related to transverse force exerted on and effecting transverse displacements of the first machine tool member along orthogonal sensor axes $x_s$ and $y_s$ that are transverse to the axis of rotation of the first machine tool member, to torque exerted on the first machine tool member about a sensor axis $z_s$ that is parallel to the axis of rotation of the first machine tool member, and to axial force exerted on and effecting axial displacement of the first machine tool member along sensor axis $z_s$.

27. The sensor of claim 26, wherein said pressure measuring means includes: a plurality of pressure transducers corresponding in number to said pressure chambers, each said pressure transducer providing an electrical output signal related to the pressure within the corresponding one of said pressure chambers; and, means for combining said electrical output signals to provide cumulative output signals respectively related to transverse force effecting displacement along said sensor axis $x_s$, to transverse force effecting displacement along said sensor axis $y_s$, to axial force effecting displacement along said sensor axis $z_s$, and to torque effecting angular displacement about said sensor axis $z_s$.

28. The sensor of claim 27, further comprising means for coupling said cumulative output signals to a stationary location.

29. The sensor of claim 27, wherein said means for coupling includes a first circuit that is rotatable with said first means and that comprises:

a first loop antenna; a source of a first RF signal; means time-multiplexing and modulating said cumulative output signals onto said first RF signal; and, means supplying said multiplexed and modulated RF signal to said first loop antenna, whereby said first loop antenna transmits a corresponding data signal.

30. The sensor of claim 29, wherein said means for coupling includes a second circuit at the stationary location that comprises:

a second loop antenna disposed in proximity to said first loop antenna; and, means responsive to said data signal as received by said second loop antenna for demultiplexing and demodulating said cumulative output signals from said first RF signal.

31. The sensor of claim 29 or claim 30, wherein said cumulative output signals are converted into corresponding pulse-width-modulated signals before modulation onto said first RF signal.

32. The sensor of claim 30, wherein said second circuit includes a source of a second RF signal and means for supplying said second RF signal to said second loop antenna, whereby said second loop antenna transmits a power signal; and, wherein said first circuit includes means responsive to said power signal as received by said loop antenna for converting said power signal into a corresponding supply voltage, and means coupling said power supply voltage to said plurality of pressure transducers, to said source of a first RF signal, and to said means for time-multiplexing and modulating said cumulative output signals onto said first RF signal.

33. The sensor of claim 20, wherein the first machine tool member is a tool holder and the second machine tool member is a tool post of the machine tool, the tool holder being mounted to and stationary relative to the tool post; wherein said first means includes means affixing said first means to the tool post so that said membranes face the tool holder; and wherein said second means includes bar means secured to said first ends of said pressure arms and means for compressing said bar means about the periphery of the tool holder so that said pressure arms are disposed about the periphery of the tool holder.

34. The sensor of claim 20, wherein the first machine tool member is a tool post of the machine tool; wherein said first means includes means affixing said first means to the tool post so that said membranes face the tool post; wherein the tool post is provided with a plurality of elongated bores corresponding in number to said pressure arms and each extending parallel to the longitudinal axis of the tool post; wherein said pressure arms are disposed within corresponding ones of said bores so that said second ends thereof project beyond the tool post; and, wherein said second means includes means for securing said first end of each of said pressure arms in the corresponding one of said bores.

35. The sensor of claim 20, wherein the second machine tool member is a tool post of the machine tool and the first machine tool member is a member that is mounted to and stationary relative to the tool post; wherein said first means includes means mounting said first means to the tool post; and wherein said pairs of pressure chambers, said membranes, and said pressure arms are arranged and disposed so that the pressures within said pressure chambers are related to force effecting displacement along orthogonal sensor axis $x_s$, $y_s$, and $z_s$.

36. A sensor responsive to displacement of a machine tool member for measuring the transverse force exerted thereon, said machine tool member being rotatable with, affixed to, and primarily supported by the spindle of a machine tool, said sensor comprising:
a receptacle module affixed to and rotatable with the spindle, said receptable module including a first pressure chamber that is filled with an incompressible fluid and that has a membrane extending transversely to a first sensor axis which is transverse to the axis of rotation of the machine tool member, a second pressure chamber that is filled with an incompressible fluid and that has a membrane extending transversely to a second sensor axis that is angularly disposed about said axis of rotation relative to said first sensor axis, and means measuring the pressure within each of said first and second pressure chambers;
first and second pressure arms, a first end of each of said pressure arms being affixed to the machine tool member at a location along said axis of rotation at which transverse force is to be measured, said first and second pressure arms extending in parallel to said axis of rotation toward said receptable module and second ends thereof respectively bearing normally on the membranes of said first and second pressure chambers, whereby the pressures within said first and second pressure chambers are related to the components of transverse force along said first and second sensor axes, respectively.

37. The sensor of claim 36, further comprising: means for measuring the angle $\theta_m$ between one of said sensor axes and a stationary axis of the machine tool; and means for combining said measured angle $\theta_m$ and the pressures measured in said first and second pressure chambers to determine the angle $\phi$ between the transverse force exerted on the machine tool member and said stationary axis.

38. The sensor of claim 37, wherein said first and second pressure arms have different lengths; wherein said first ends of said first and second pressure arms are affixed to the machine tool member at spaced locations along said axis of rotation; and, further comprising means for combining said measured angle $\theta_m$, the pressures measured in said first and second pressure chambers, and said determined angle $\phi$ to determine the plane of transverse loading of the transverse force exerted on the machine tool member.

39. The sensor of claim 38, further comprising means for compensating the pressures measured in said first and second pressure chambers in accordance with said determined plane of transverse loading.

* * * * *

UNITED STATES PATENT AND TRADEMARK OFFICE
CERTIFICATE OF CORRECTION

PATENT NO. : 4,444,061
DATED : April 24, 1984
INVENTOR(S) : Richard A. Mathias

It is certified that error appears in the above-identified patent and that said Letters Patent is hereby corrected as shown below:

| | | |
|---|---|---|
| Abstract, | line 12: | Insert --,--(comma) after "force" |
| Column 2, | line 4: | Insert --of-- after "type" |
| Column 4, | line 34: | Insert --that extends-- after "portion" |
| Column 5, | line 29: | "or" should be --of-- |
| Column 9, | line 11: | Insert --a-- after "is" |
| Column 10, | line 36: | Delete --,-- (comma) after "arms" |
| Column 14, | line 15: | Insert --module 60-- after "receptacle" |
| | line 44: | "theaded" should be --threaded-- |
| Column 16, | line 10: | "32MIa" should be --$32Ml_a$-- |
| Column 17, | line 18: | "$PS_{67A}$" should be --$PS\,\delta_A$-- |
| Column 18, | line 60: | "plant" should be --plane-- |
| Column 23, | line 32: | "content" should be --contact-- |
| Column 25, | line 9: | "is" should be --it-- |
| Column 31, | line 33: | "axis" should be --axes-- |
| | line 41: | "receptable" should be --receptacle-- |
| Column 32, | line 14: | "receptable" should be --receptacle-- |

Signed and Sealed this

Twenty-fifth Day of September 1984

[SEAL]

Attest:

GERALD J. MOSSINGHOFF

Attesting Officer   Commissioner of Patents and Trademarks